United States Patent [19]
Tollini

[11] Patent Number: 5,397,639
[45] Date of Patent: Mar. 14, 1995

[54] SECURING TAPE

[76] Inventor: Dennis R. Tollini, 12 Palmdale Dr., Williamsville, N.Y. 14221

[21] Appl. No.: 140,232

[22] Filed: Oct. 20, 1993

Related U.S. Application Data

[63] Continuation-in-part of Ser. No. 981,506, Nov. 25, 1992, Pat. No. 5,266,401.

[51] Int. Cl.⁶ .................... B32B 7/12; A61M 25/02
[52] U.S. Cl. .................... 428/343; 428/230; 428/231; 428/354; 128/DIG. 6; 128/DIG. 26; 128/877; 604/174; 604/179; 604/180
[58] Field of Search ............ 428/343, 354, 230, 231; 128/DIG. 6, DIG. 26, 877; 604/174, 180, 179

[56] References Cited

U.S. PATENT DOCUMENTS

| | | | |
|---|---|---|---|
| 3,288,136 | 11/1966 | Lund | 128/133 |
| 3,430,300 | 3/1969 | Doan | 604/180 X |
| 3,556,096 | 1/1971 | Fuller | 128/171 |
| 3,823,713 | 7/1974 | Shah | 128/157 |
| 3,826,254 | 7/1974 | Mellor | 128/133 |
| 3,834,380 | 9/1974 | Boyd | 128/133 |
| 4,165,748 | 8/1979 | Johnson | 128/343 |
| 4,263,906 | 4/1981 | Finley | 128/157 |
| 4,324,237 | 4/1982 | Buttaravoli | 604/180 |
| 4,457,754 | 7/1984 | Buttaravoli | 128/DIG. 26 |
| 4,569,348 | 2/1986 | Hasslinger | 604/179 |
| 4,662,366 | 5/1987 | Tari | 128/877 |
| 4,671,787 | 6/1987 | Widman | 128/DIG. 26 |
| 4,702,736 | 10/1987 | Kalt et al. | 604/180 |
| 4,732,146 | 3/1988 | Fasline et al. | 128/155 |
| 4,737,143 | 4/1988 | Russell | 128/DIG. 26 |
| 4,738,662 | 4/1988 | Kalt et al. | 604/180 |
| 4,822,342 | 4/1989 | Brawner | 604/180 |
| 4,838,878 | 6/1989 | Kalt et al. | 604/180 |
| 4,909,243 | 3/1990 | Frank et al. | 128/156 |
| 4,928,712 | 5/1990 | Mele | 128/877 |
| 4,976,700 | 12/1990 | Tollini | 604/180 |
| 5,098,399 | 3/1992 | Tollini | 604/180 |
| 5,147,322 | 9/1992 | Bowen et al. | 604/180 |
| 5,244,523 | 9/1993 | Tollini | 156/227 |
| 5,266,401 | 11/1993 | Tollini | 428/343 |

FOREIGN PATENT DOCUMENTS 8606641 11/1986 WIPO .................... 604/180

Primary Examiner—Daniel R. Zirker
Attorney, Agent, or Firm—Joseph P. Gastel

[57] ABSTRACT

A securing tape for securement to a foreign body including an elongated tape having first and second sides, a base portion on the tape, adhesive on the first side of the tape for securing the base portion to a foreign body, a tab having a fixed end and a free end with the tab being formed by cutting it out of the tape while leaving the fixed end integrally attached to the base portion, an opening in the base portion being formed in the location from which the tab was cut of the tape, an outer end on the opening remote from the fixed end of the tab, a relocating arrangement for effectively relocating the free end of the tab and the outer end of the opening relative to each other to permit the free end of the tab to be secured relative to the base portion, and securing structure for securing the free end of the tab to the base portion.

27 Claims, 18 Drawing Sheets

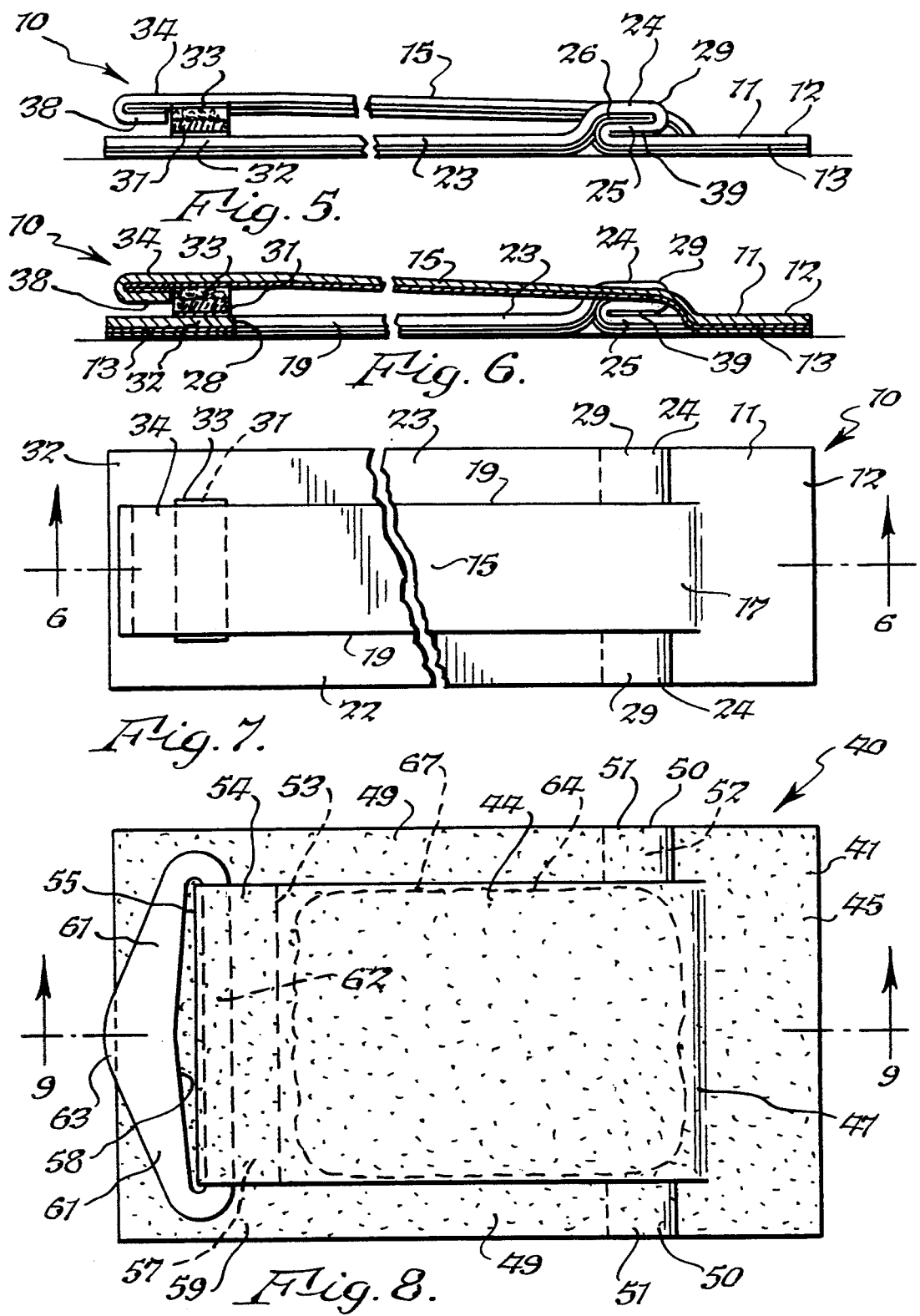

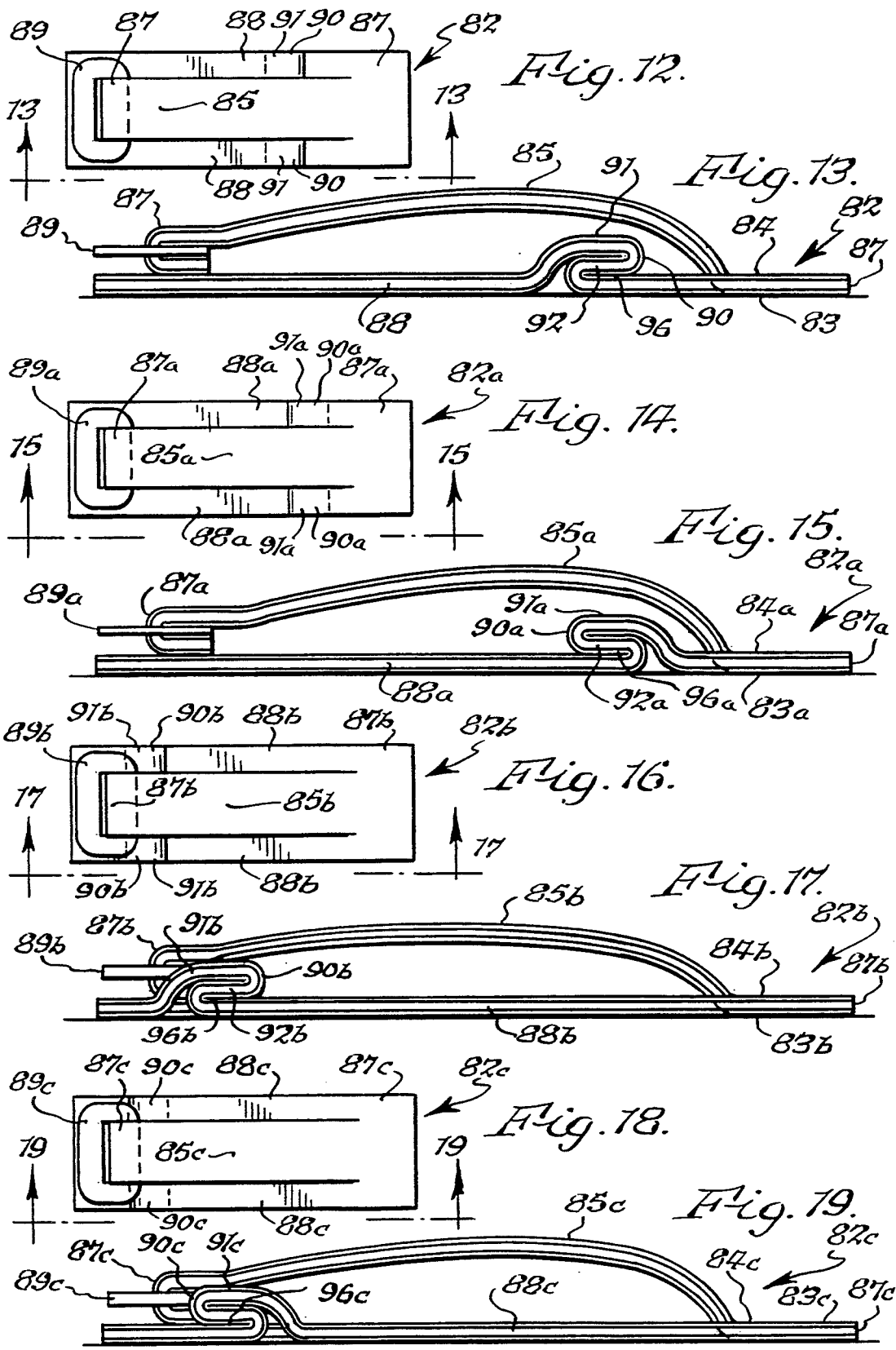

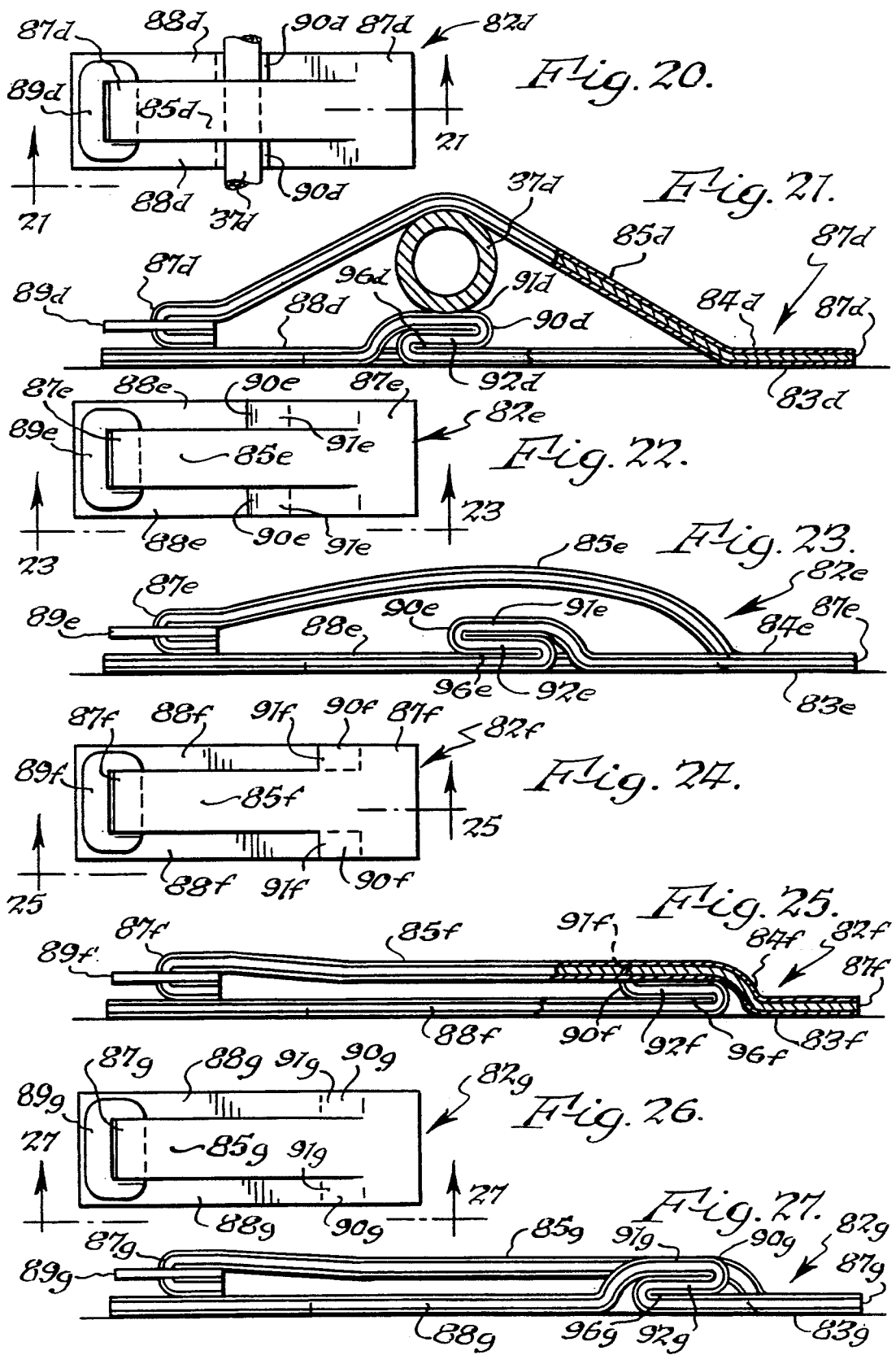

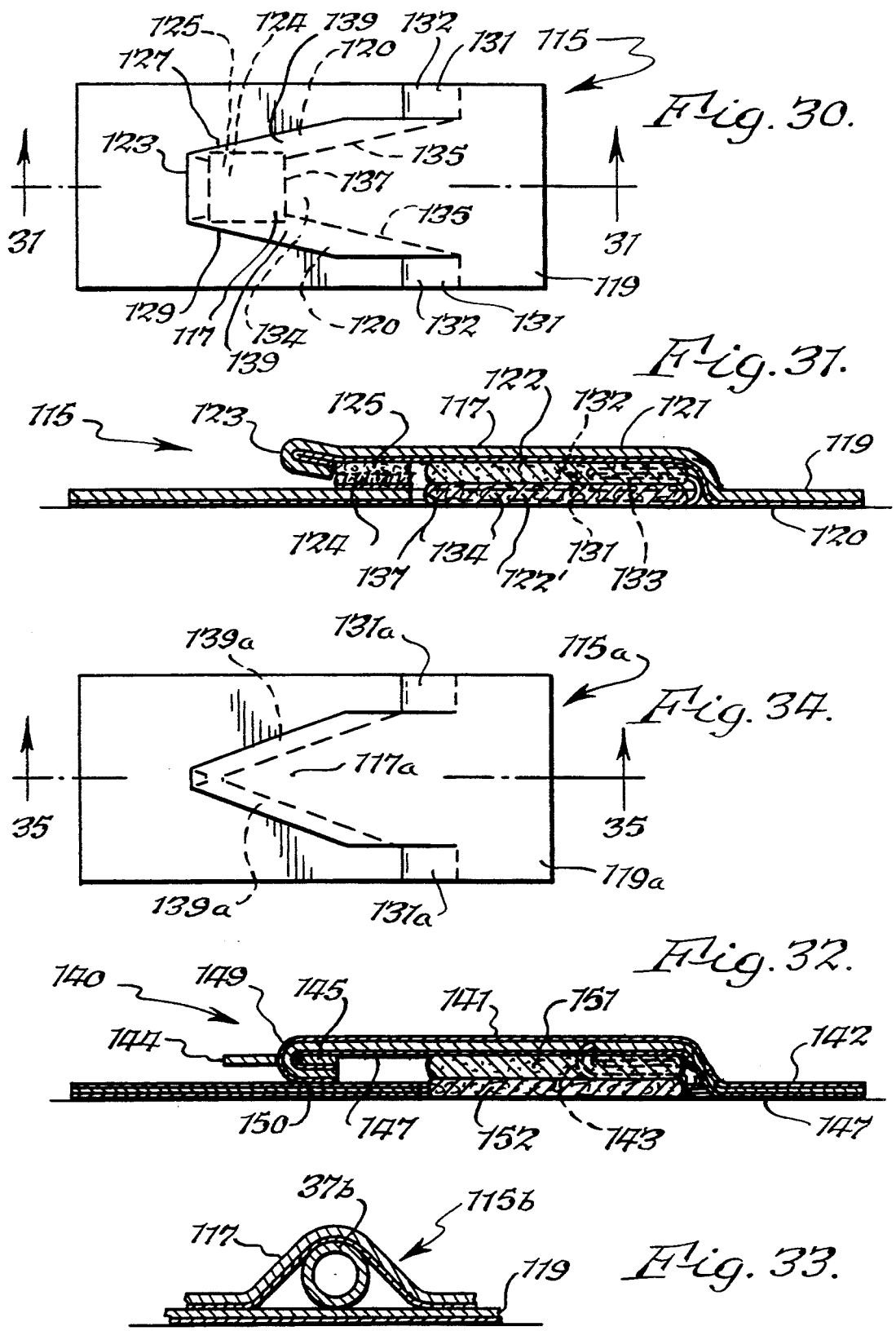

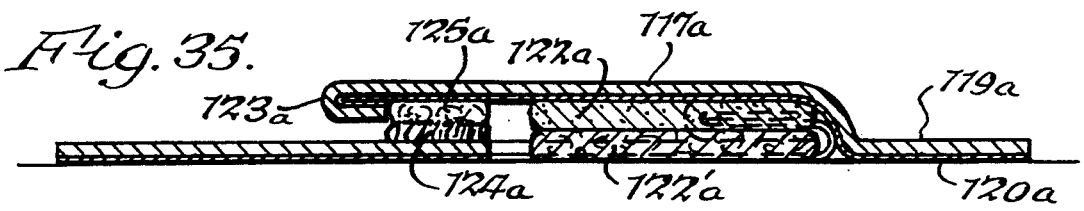
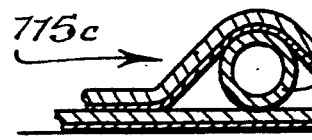
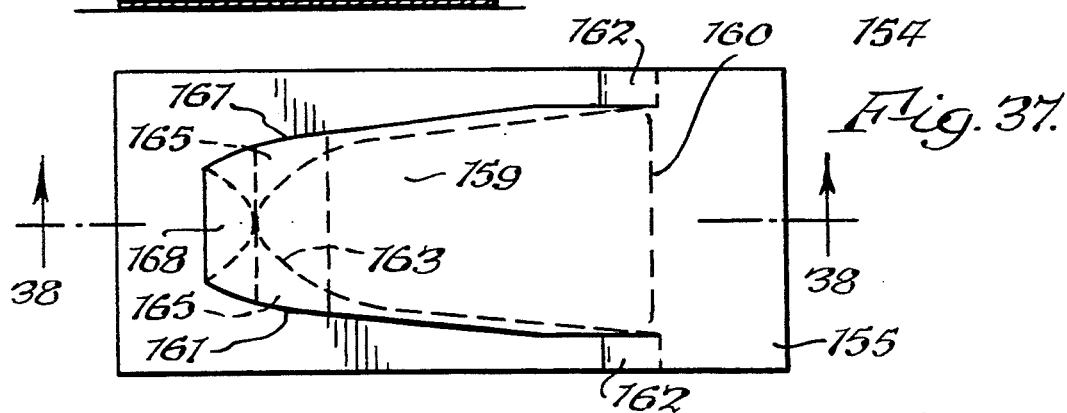
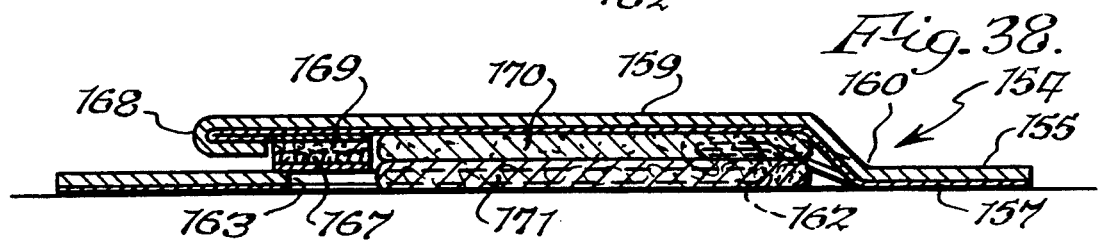
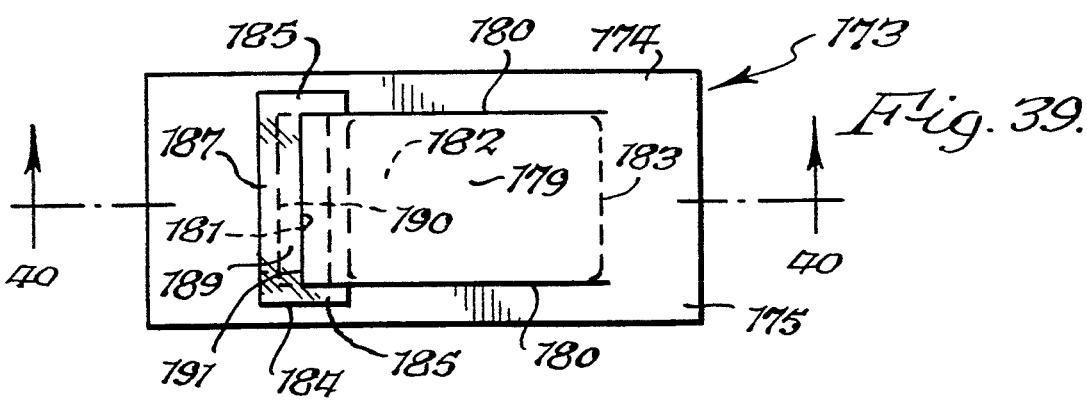
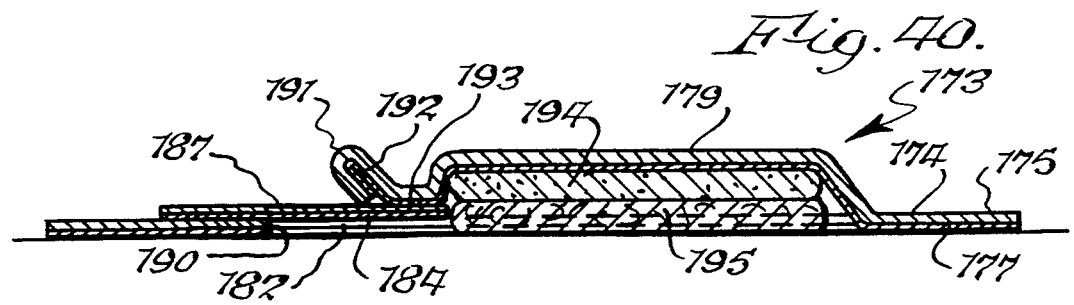

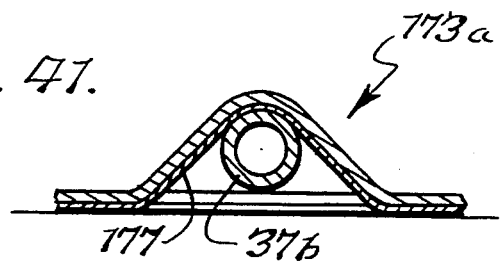
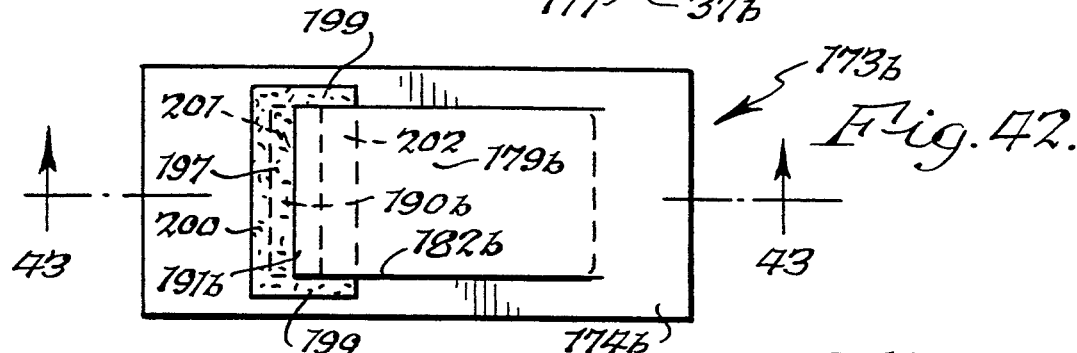
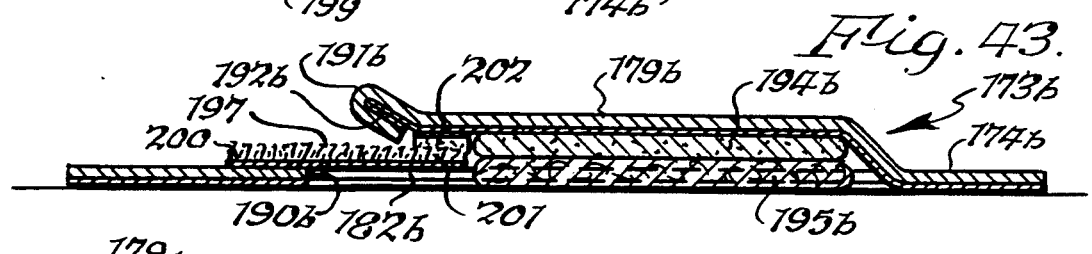
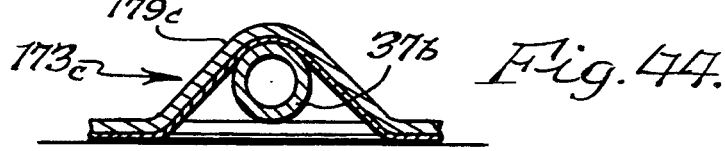
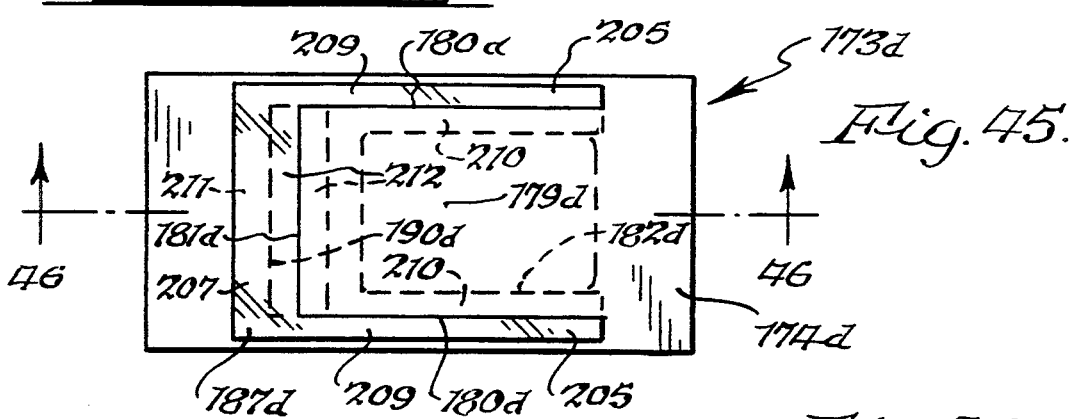
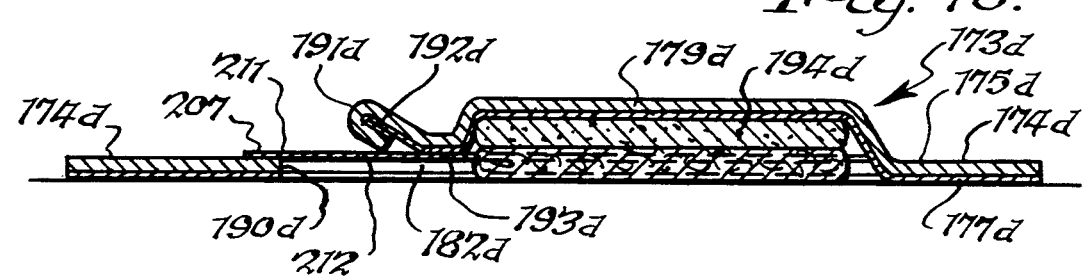

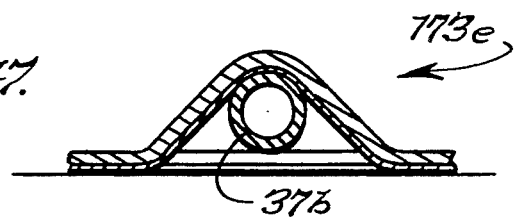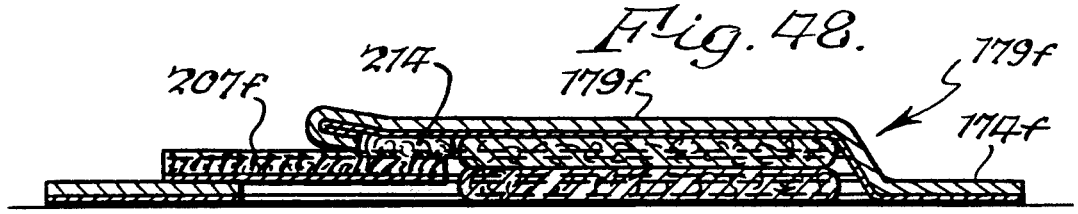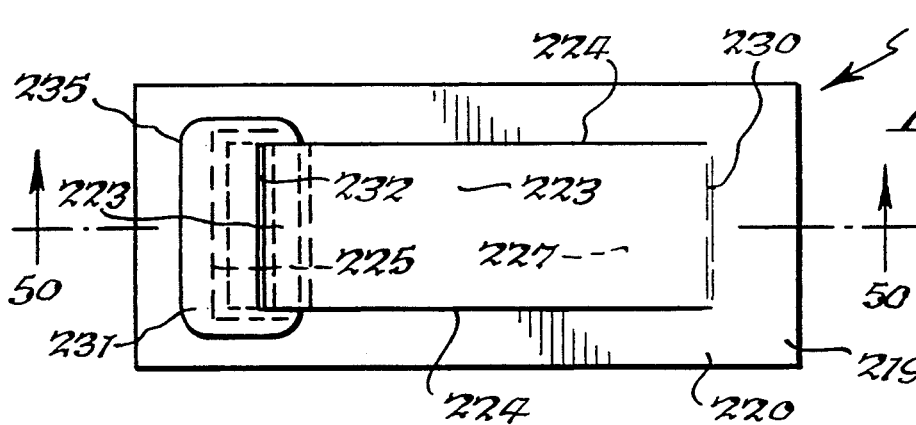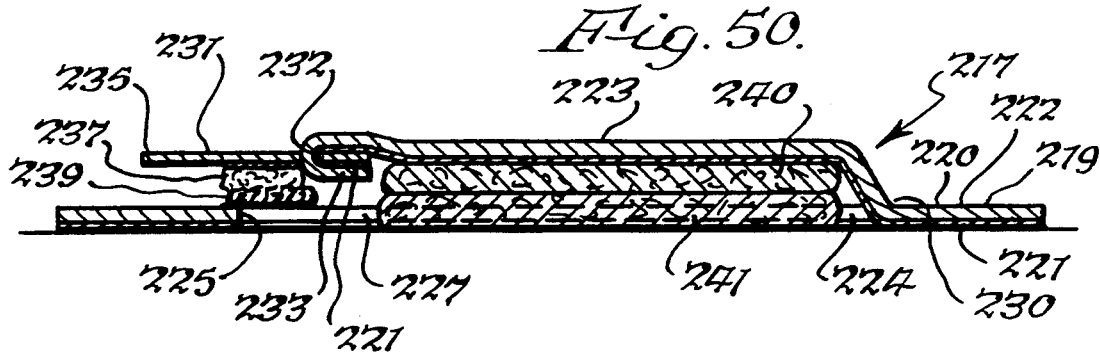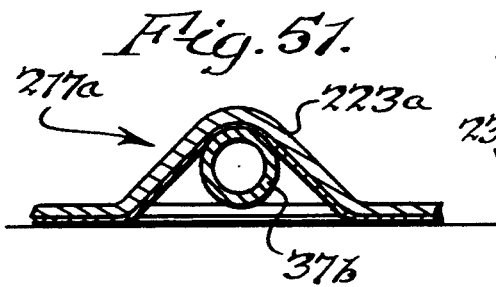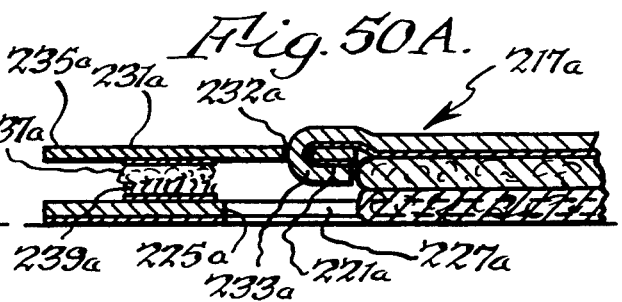

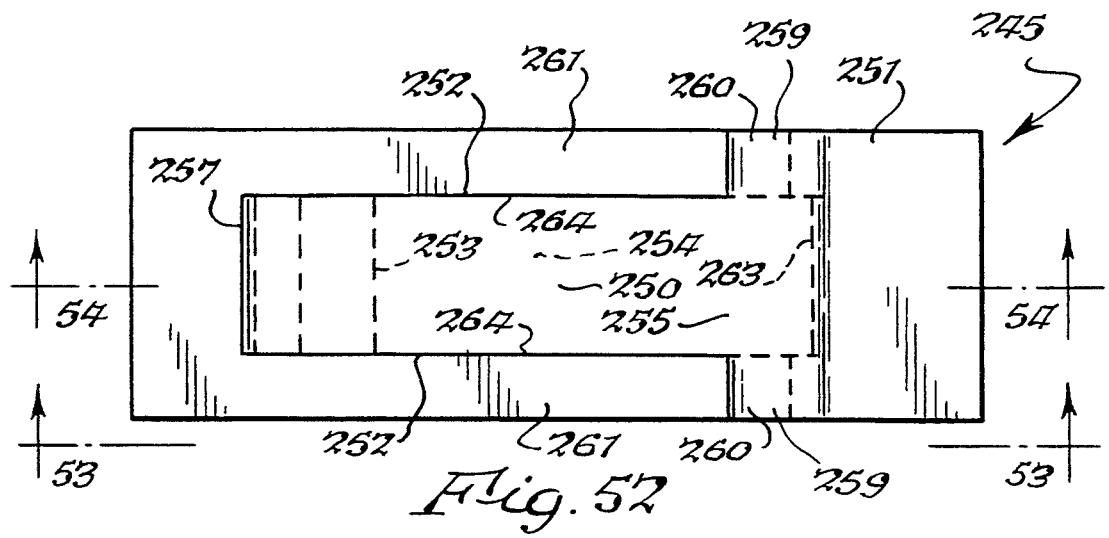
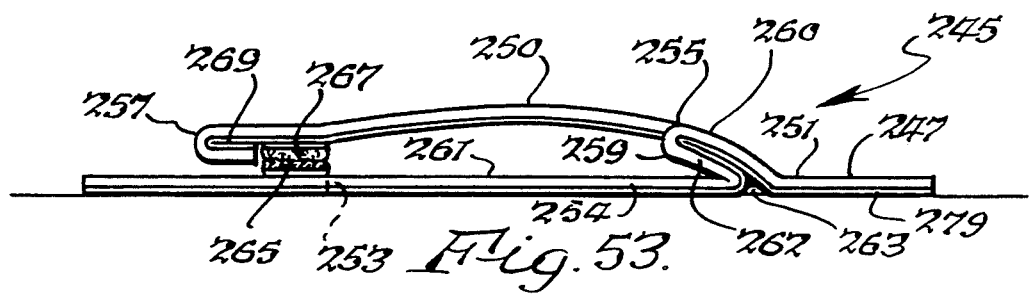
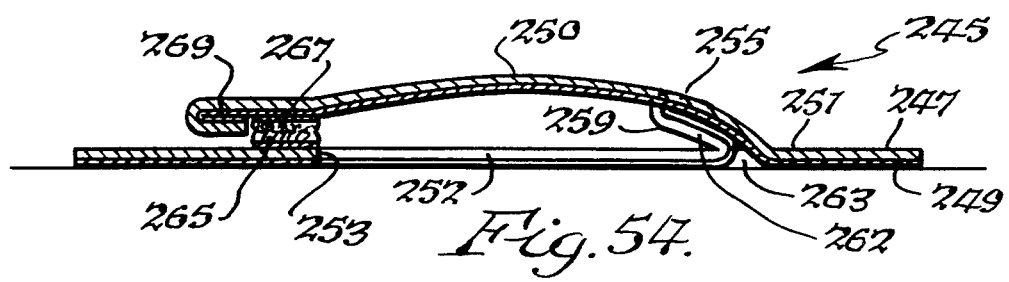
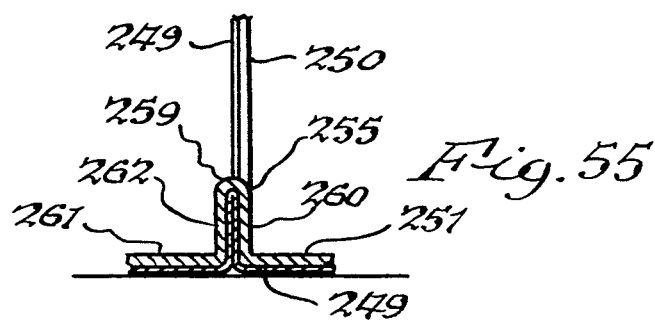

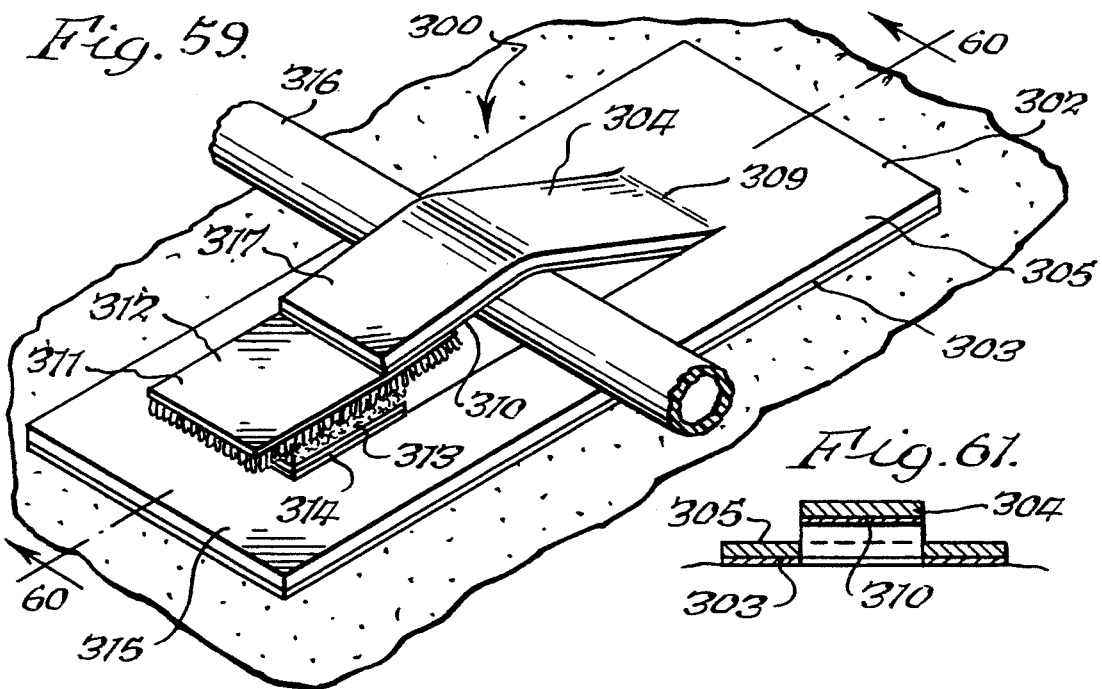
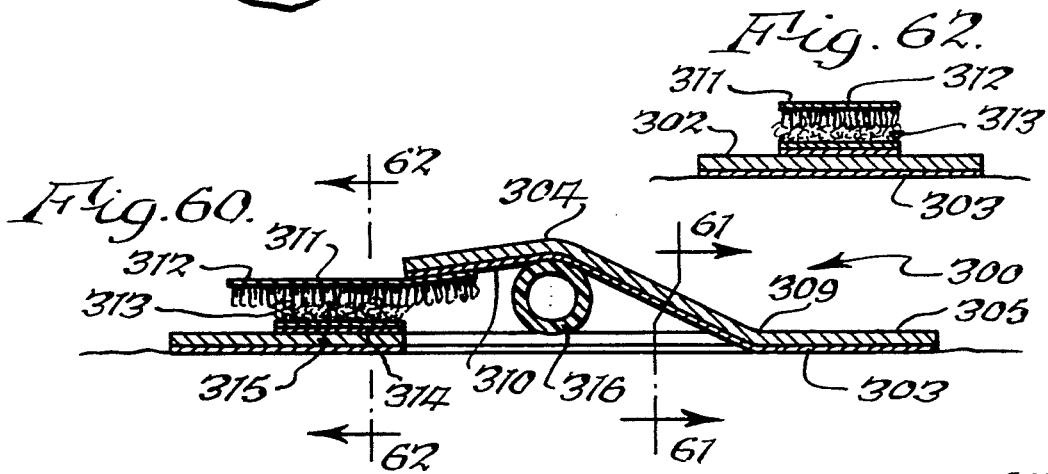
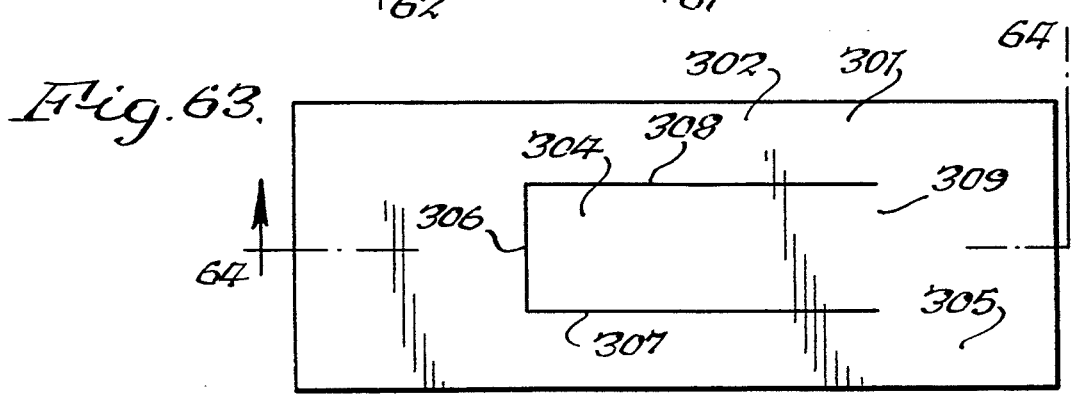
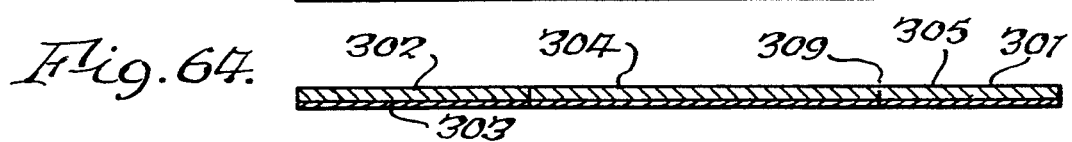

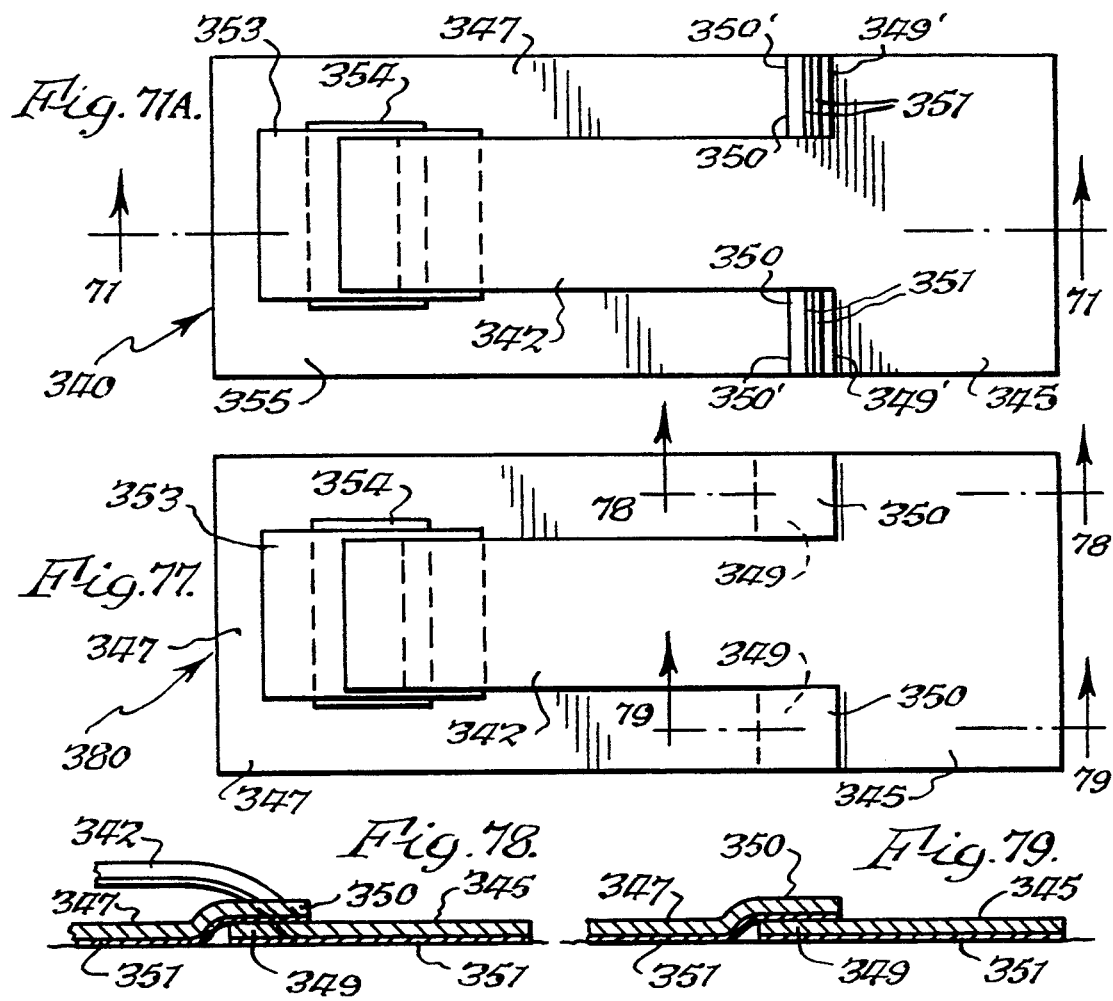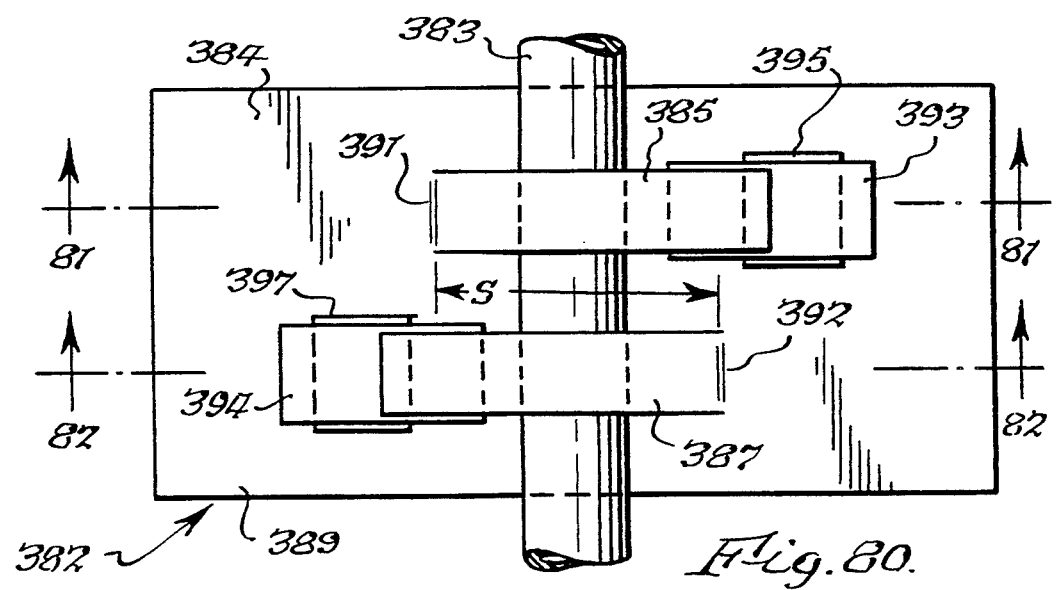

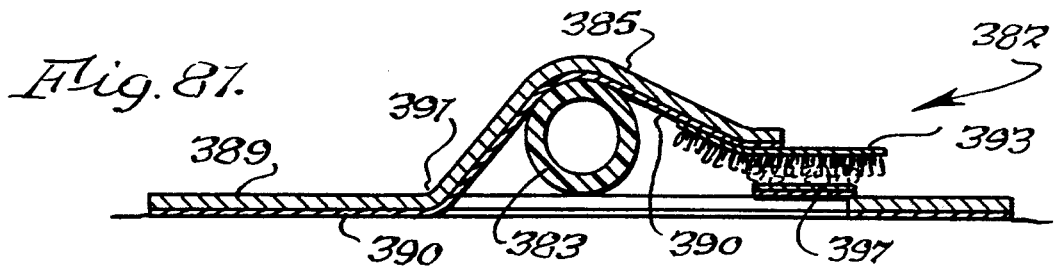
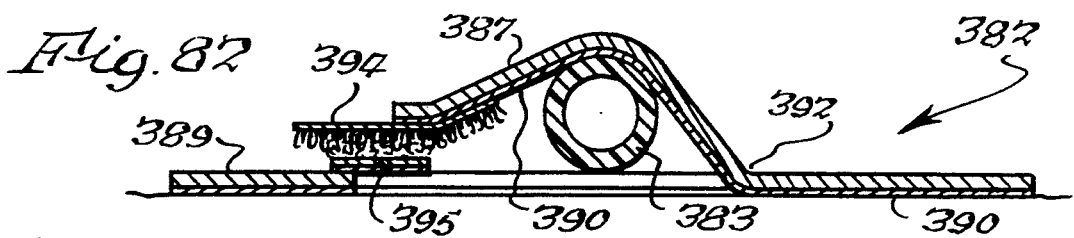
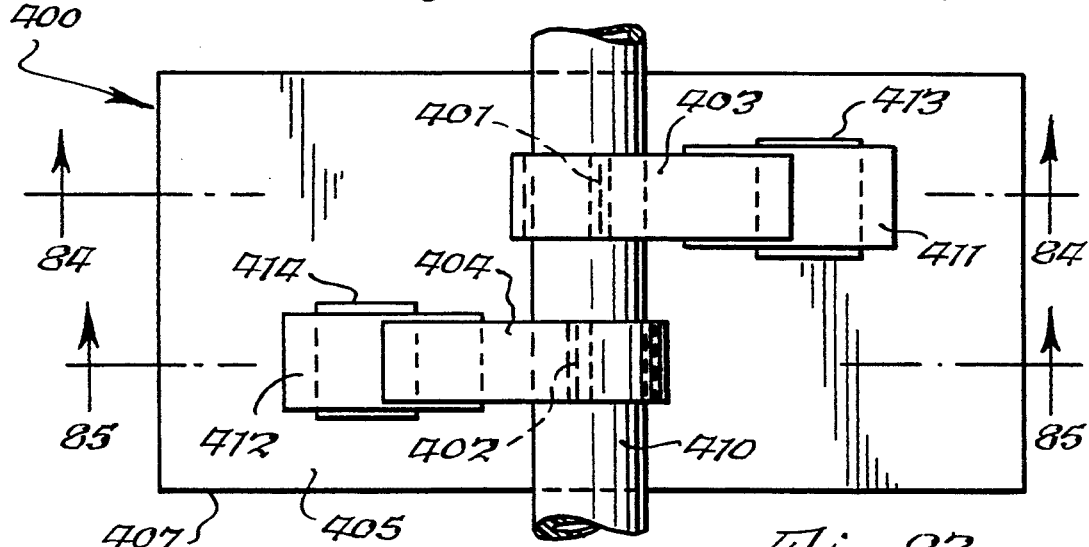
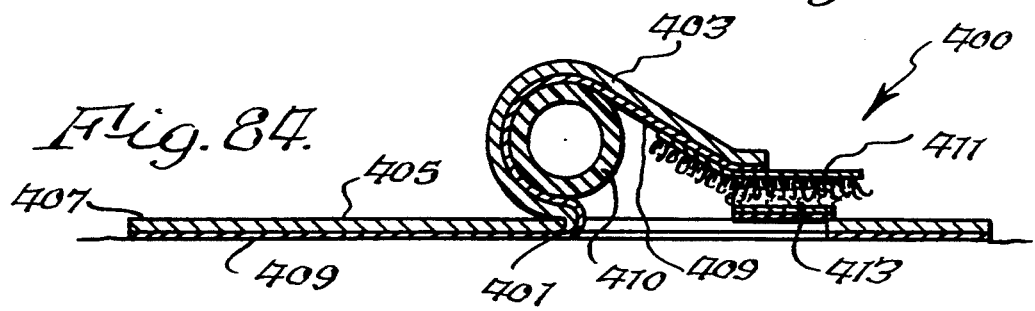
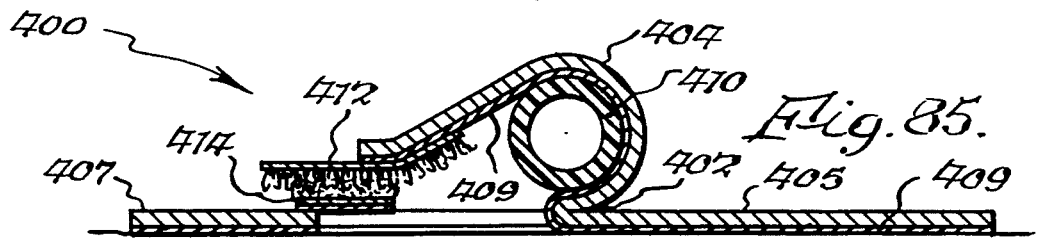

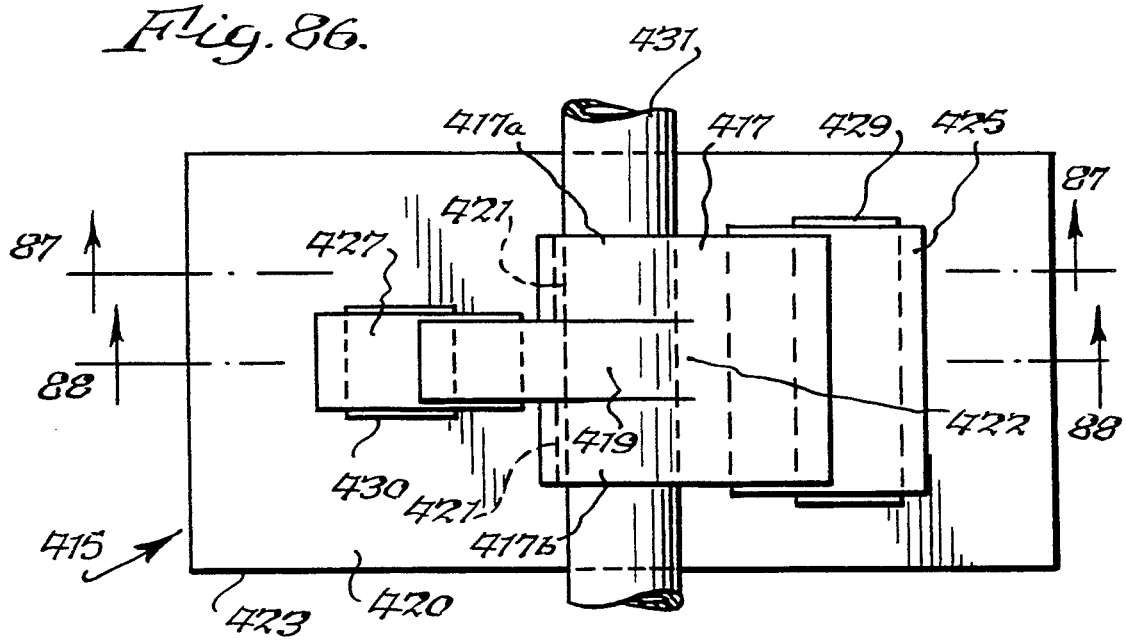
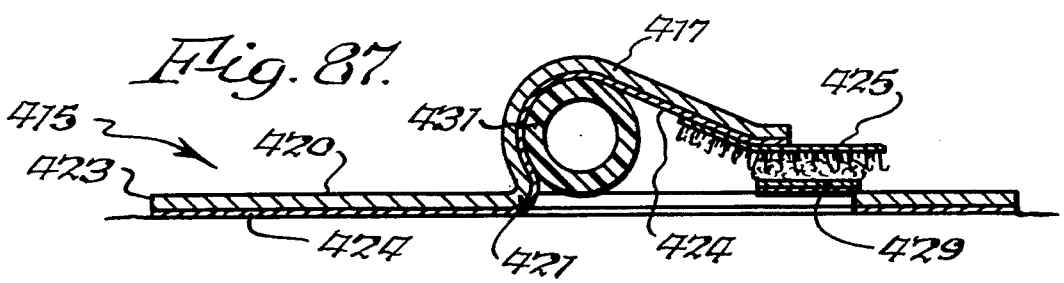
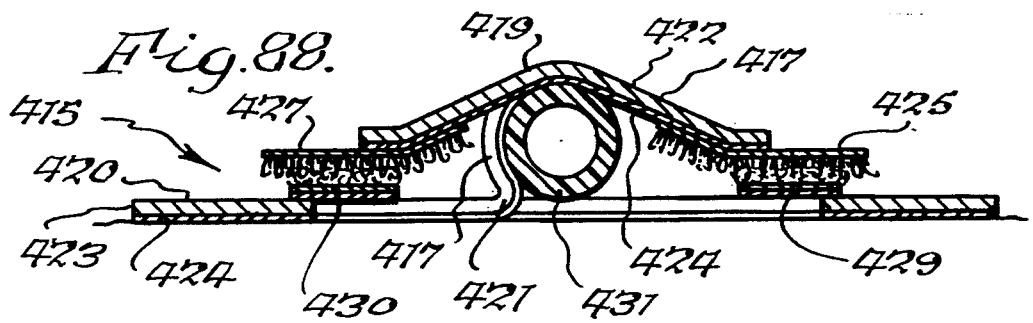

SECURING TAPE

CROSS REFERENCE TO RELATED APPLICATION

The present application is a continuation-in-part of application Ser. No. 07/981,506, filed Nov. 25, 1992, now U.S. Pat. No. 5,266,401, issued Nov. 30, 1993.

BACKGROUND OF THE INVENTION

The present invention relates to an improved securing tape for securing an object to a foreign body and more particularly a securing tape in the form of a bandage for securing a dressing to a patient and a securing tape for securing a medical device, such as tubing, a catheter, an intravenous needle, or the like, to a patient's skin or to another support.

By way of background, in my previous U.S. Pat. Nos. 4,976,700 and 5,098,399 and my pending application Ser. No. 834,583, filed Feb. 12, 1992, various embodiments of securing tapes were fabricated of single pieces of tape and had tabs which were of double thickness and thus required a relatively large amount of tape from which they were formed.

SUMMARY OF THE INVENTION

It is one object of the present invention to provide a securing tape formed of a single piece of material wherein a tab is formed integrally with a base portion and utilizes less tape material than previous embodiments utilizing a tab which was of double thickness.

Another object of the present invention is to provide an improved securing tape having an integral single thickness tab and unique ways of causing the free end of the tab to be secured to the base portion of the securing tape. Other objects and attendant advantages of the present invention will readily be perceived hereafter.

The present invention relates to various embodiments of a securing tape for securement to a foreign body, each embodiment comprising an elongated tape having first and second sides, a base portion on said tape, adhesive means on said first side of said tape for securing said base portion to a foreign body, a tab having a fixed end and a free end, said tab being formed by cutting it out of said tape while leaving said fixed end integrally attached to said base portion, an opening in said base portion, said opening being formed in the location from which said tab was cut out of said tape, an outer end on said opening remote from said fixed end of said tab, relocating means for effectively relocating said free end of said tab and said outer end of said opening relative to each other to permit said free end of said tab to be secured relative to said base portion, and securing means for securing said free end of said tab to said base portion. Certain of the embodiments utilize securing means which constitutes the adhesive means on the tape itself. Other embodiments utilize securing means which are adhesively secured to the base portion and/or tab by the use of the adhesive means of the tape itself. Another embodiment relocates the free end of the tab and the opening relative to each other by cutting the base portion of the tape crosswise proximate the fixed end of the tab to create tabs which are secured to each other in face-to-face relationship.

The present invention will be more fully understood when the following portions of the specification are read in conjunction with the accompanying drawings wherein:

BRIEF DESCRIPTION OF THE DRAWINGS

FIG. 5 is a fragmentary side elevational view of the securing tape of FIG. 1;

FIG. 6 is a fragmentary longitudinal cross sectional view of the tape of FIG. 5 taken substantially along line 6—6 of FIG. 7;

FIG. 7 is a fragmentary plan view of the securing tape of FIG. 5;

FIG. 8 is a plan view of a securing tape in the form of a bandage for holding a dressing against a wound which incorporates the same principles of construction of the embodiments of FIGS. 1-7 and which utilizes a self-adhering fabric, thereby eliminating the use of hook and pile fasteners;

FIG. 12 is a reduced plan view of still another embodiment of the securing tape which utilizes self-adhering fabric, thereby eliminating the use of hook and pile fabric;

FIG. 13 is a side elevational view taken substantially in the direction of arrows 13—13 of FIG. 12;

FIG. 14 is a reduced plan of another embodiment of a securing tape utilizing self-adhering fabric;

FIG. 15 is a side elevational view taken substantially in the direction of arrows 15—15 of FIG. 14;

FIG. 16 is a reduced plan view of still another embodiment of the securing tape using self-adhering fabric;

FIG. 17 is a side elevational view taken substantially in the direction of arrows 17—17 of FIG. 16;

FIG. 18 is a reduced plan view of still another embodiment of securing tape utilizing self-adhering fabric;

FIG. 19 is a side elevational view taken substantially in the direction of arrows 19—19 of FIG. 18;

FIG. 20 is a fragmentary plan view of still another embodiment of a securing tape utilizing self-adhering fabric;

FIG. 21 is a view, partially in cross section, taken substantially along line 21—21 of FIG. 20;

FIG. 22 is a reduced plan view of still another embodiment of a medical securing tape utilizing self-adhering fabric;

FIG. 23 is a side elevational view taken substantially in the direction of arrows 23—23 of FIG. 22;

FIG. 24 is a reduced plan view of still another embodiment of a securing tape utilizing self-adhering fabric;

FIG. 25 is a cross sectional view taken substantially along line 25—25 of FIG. 24;

FIG. 26 is a reduced plan view of still another embodiment of a securing tape utilizing self-adhering fabric;

FIG. 27 is a side elevational view taken substantially in the direction of arrows 27—27 of FIG. 26;

FIG. 30 is a plan view of still another embodiment of the present invention which can be utilized as a bandage and which has the advantage of providing adhesion between three sides of the tab and the base because of the trapezoidal shape of the tab;

FIG. 31 is a cross sectional view taken substantially along line 31—31 of FIG. 30;

FIG. 32 is a cross sectional view of another embodiment which utilizes the same blank as shown in FIG. 30 and is identical in all respects except that it is fabricated out of self-adhering fabric so that the use of hook and pile fabric is eliminated;

FIG. 33 is a cross sectional view similar to FIG. 31 but showing the embodiment of FIG. 31 utilized as a securing tape for a tubing;

FIG. 34 is a plan view of a modified form of the embodiment of FIG. 30 which utilizes a substantially triangular tab rather than a trapezoidal tab;

FIG. 35 is a cross sectional view taken substantially along line 35—35 of FIG. 34;

FIG. 36 is a fragmentary cross sectional view showing the embodiment of FIG. 34 utilized as a securing tape for a tubing;

FIG. 37 is a modified embodiment of the configuration shown in FIG. 30 wherein the tab is curved throughout its length;

FIG. 38 is a cross sectional view taken substantially along line 38—38 of FIG. 37;

FIG. 39 is a plan view of still another embodiment of the securing tape of the present invention in the form of a bandage having a base material with a pressure-sensitive adhesive face which will stick strongly to practically anything including silicone surfaces but will stick repeatedly and releasably to MYLAR-like material so that the end of the tab can be removed and replaced from the MYLAR-like material without leaving a residue of adhesive;

FIG. 40 is a cross sectional view taken substantially along line 40—40 of FIG. 39;

FIG. 41 is a cross sectional view of a modified embodiment of FIG. 39 which is used as a securing tape because the compression pad has been removed from the tab;

FIG. 42 is a plan view of a bandage utilizing a similar blank as shown in FIG. 39 but which does not utilize the type of material of FIG. 39 but instead uses hook and pile fabric at the end of the tab which overlies the opening in the base portion;

FIG. 43 is a cross sectional view taken substantially along line 43—43 of FIG. 42 and showing the bandage utilized in conjunction with a dressing;

FIG. 44 is a cross sectional view similar to FIG. 43 but showing the blank of FIG. 42 utilized as a securing tape;

FIG. 45 is a plan view of a bandage utilizing the materials of FIG. 39 in a configuration which permits the tab to adhere to the base on three sides;

FIG. 46 is a cross sectional view taken substantially along line 46—46 of FIG. 45;

FIG. 47 is a cross sectional view similar to FIG. 46 but showing the tape of FIG. 45 utilized as a securing tape rather than a bandage;

FIG. 48 is a plan view of a bandage having the same configuration as that of FIG. 45 but showing the adhering surfaces as being formed of VELCRO;

FIG. 49 is a plan view of another embodiment of the present invention wherein the tab is extended beyond the opening by means of a finger piece and mating VELCRO is secured between the finger piece and the base;

FIG. 50 is a cross sectional view of the bandage taken along line 50—50 of FIG. 49;

FIG. 50A is a fragmentary cross sectional view of a modification of the embodiment of FIG. 49;

FIG. 51 is a cross sectional view similar to FIG. 50 but showing the embodiment of FIG. 49 used as a securing tape;

FIG. 52 is a plan view of another embodiment of the present invention wherein the tab is an integral extension of the base and the borders of the base adjacent the fixed end of the base are folded back under the adjacent portion of the base;

FIG. 53 is a side elevational view taken substantially in the direction of the arrows 53—53 of FIG. 2;

FIG. 54 is a cross sectional view taken substantially along lines 54—54 of FIG. 52;

FIG. 55 is a fragmentary side elevational view of the tab of the embodiment of FIG. 52 in a raised position.

FIG. 59 is a fragmentary perspective view of another embodiment of the present invention;

FIG. 60 is a cross sectional view taken substantially along line 60—60 of FIG. 59;

FIG. 61 is a cross sectional view taken substantially along line 61—61 of FIG. 60;

FIG. 62 is a cross sectional view taken substantially along line 62—62 of FIG. 60;

FIG. 63 is a plan view of the blank which is used to make the embodiment of FIG. 59;

FIG. 64 is a cross sectional view taken substantially along line 64—64 of FIG. 63;

FIG. 71A is a plan view of the embodiment of FIG. 71;

FIG. 76 is a cross sectional view taken substantially along line 76—76 of FIG. 74;

FIG. 77 is a plan view of another embodiment which is made from the blank of FIG. 70;

FIG. 78 is a fragmentary cross sectional view taken substantially along line 78—78 of FIG. 77;

FIG. 79 is a fragmentary cross sectional view taken substantially along line 79—79 of FIG. 77;

FIG. 80 is a plan view of still another embodiment of the present invention which utilizes tabs which cross over the object to be held from opposite directions;

FIG. 81 is a cross sectional view taken substantially along line 81—81 of FIG. 80;

FIG. 82 is a cross sectional view taken substantially along line 82—82 of FIG. 80;

FIG. 83 is a plan view similar to FIG. 80 but showing a modification of the embodiment of FIG. 80;

FIG. 84 is a cross sectional view taken substantially along line 84—84 of FIG. 83;

FIG. 85 is a cross sectional view taken substantially along line 85—85 of FIG. 83;

FIG. 86 is a plan view of still another embodiment of the general type of FIGS. 80 and 83;

FIG. 87 is a cross sectional view taken substantially along line 87—87 of FIG. 86; and FIG. 88 is a cross sectional view taken substantially along line 88—88 of FIG. 86.

DESCRIPTION OF THE PREFERRED EMBODIMENTS

Figure 1:
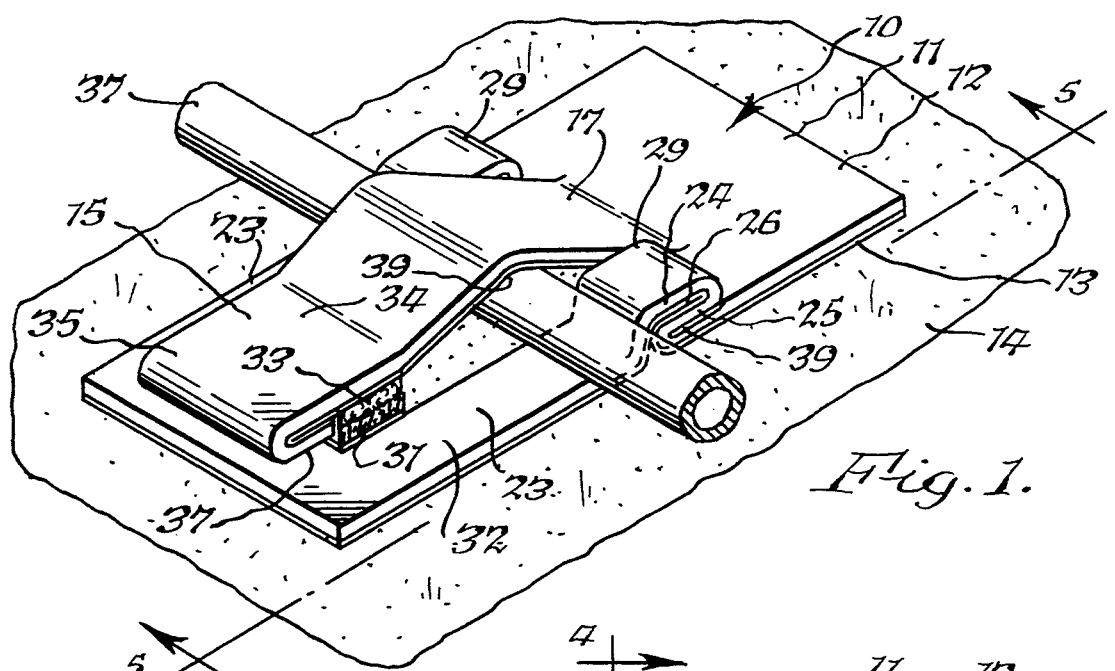
FIG. 1 is a fragmentary perspective view of a medical securing tape in position on a patient's skin or support and holding a medical device such as a tube or catheter.

In FIGS. 1-7 one embodiment of a medical securing tape of the present invention is shown. The securing tape 10 is shown having a base 11 with a nonadhesive outer surface 12 and a pressure-sensitive adhesive surface 13 for attachment to a body 14 which may be a patient or any other surface to which tape 11 is to be secured. A tab 15 has an end 17 which is an integral extension of the base 11 and which is formed by cutting it from base portion along lines 19, 20 and 21 shown in FIG. 2, which is a plan view of the blank piece of tape from which the securing tape 10 is formed. As can be seen from FIG. 2, when tab 15 is lifted upwardly out of the plane of the paper, an opening 22 is formed in base 11, and the opening lies between elongated side portions 23 of base 11.

Figure 2:
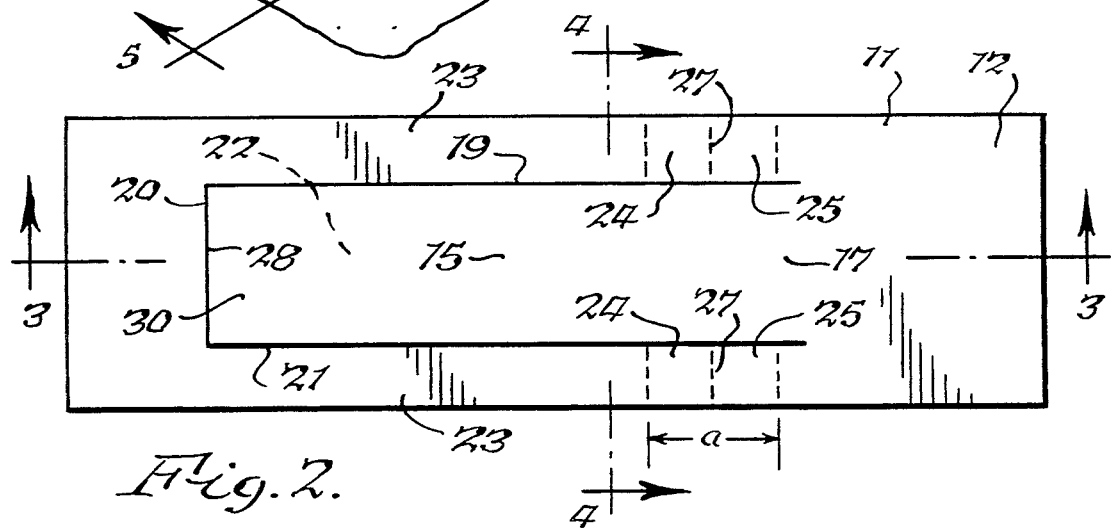
FIG. 2 is a plan view of the blank which is utilized in fabricating the medical securing tape of FIG. 1.
Figure 3:
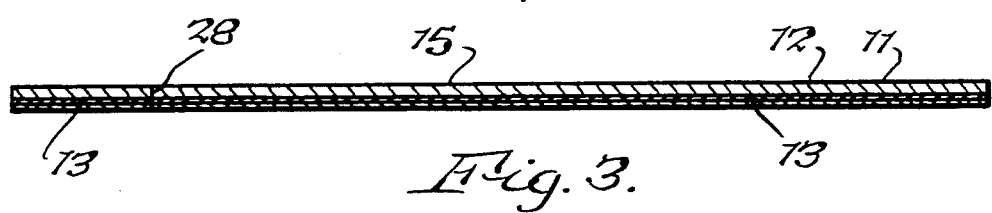
FIG. 3 is a cross sectional view taken substantially along line 3—3 of FIG. 2.
Figure 4:
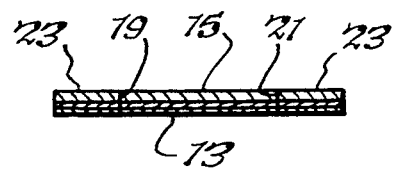
FIG. 4 is a cross sectional view taken substantially along line 4—4 of FIG. 2.

In order to form securing tape 10 from the blank shown in FIGS. 2, 3 and 4, the side portions 23 are folded as shown in FIGS. 1, 5, 6 and 7. In this respect, the portions 24 and 25 (FIG. 2) are folded toward each other along fold lines 27, and thus the pressure-sensitive adhesive 13 underlying these portions will cause them to adhere to each other as at 26 (FIGS. 1 and 5). Thus the adhered portions 24 and 25 will form folds 29 which effectively shortens the length of opening 22 by the length a (FIG. 2). In other words, after the fold 29 has been made, the end 30 of tab 15 is relocated relative to the opening and it will extend beyond the edge 28 of opening 22 by the length a. Hook fabric 31 is then adhesively secured to end portion 32 of base 11, and pile fabric 33 is adhesively secured to the end portion 34 of tab 15. The portion 35 beyond pile fabric 33 is folded under to cover the pressure-sensitive adhesive on the underside of the end of tab 15 and thus provide a portion which can be grasped to disengage the hook and pile fabric portions 31 and 33. In FIG. 1 the tab 15 is shown in the closed position holding a tube or catheter 37 down onto base 11, and the pressure-sensitive adhesive on the underside of tab 15 at 39 firmly secures tube 37 in position. It will be appreciated that the hook and pile fabric portions 31 and 33 can be separated to remove tube 37 and thereafter reconnected to replace tube 37, as desired.

The folds 29 are shown in FIGS. 1 and 5-7 as lying horizontally on the base portion. This can be effected by either causing them to be adhesively attached at 39 or by a spot heat-seal or the like. However, causing it to lie horizontally is not really necessary but is strictly optional. In FIG. 7A the structure is identical to that shown in FIGS. 1 and 5-7 except that fold 29 has not been laid down horizontally. It will be appreciated that the dimensions, especially the thickness portions of the securing tape 11, have been exaggerated for purposes of illustration.

Figure 9:
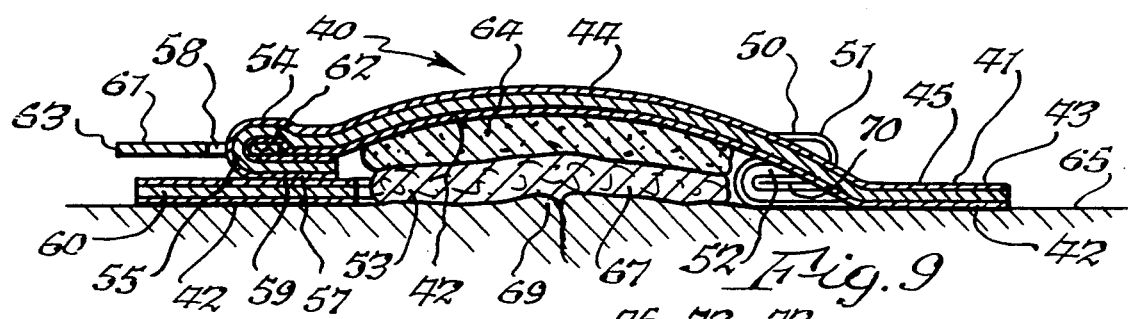
FIG. 9 is a cross sectional view taken substantially along line 9—9 of FIG. 8 and showing the bandage in position on a patient's skin and holding a dressing in place against a wound.

In FIGS. 8 and 9 the above principles of relocating the tab and the opening of a tape relative to each other by creating folds are applied to a securing tape in the form of a bandage for holding a dressing. In this respect, the bandage 40 is formed from a tape 41 having a pressure-sensitive adhesive surface 42 throughout its length and an outer self-adhering surface 43, which is a surface which can adhere to itself but which does not adhere to other objects. The self-adhering surface is basically a combination of hook and pile fabric wherein the hook portions and pile portions are interspersed with each other to form a nap which is of much less height than the nap of convention hook fabric and pile fabric. In the bandage 40 the tab 44 is integrally attached to base portion 45 at 47. The sides 49 on opposite sides of tab 44 are folded over on themselves to form folds 50 consisting of upper portions 51 and lower portions 52. This causes the opening 53 from which tab 44 was cut to be foreshortened. The end portion 54 of tab 44 is turned over on itself at 55 so that the self-adhering fabric on surface 57 can be attached to the self-adhering fabric 59 on base portion 60. A handle 61 has slot 58 therein through which the end portion 54 of the tab is threaded. A portion 62 of handle 61 is held in end portion 54 of tab 44, and the outer portion 63 of handle 61 can be grasped to disengage adhering tape portions 57 and 59. A self-adhering fabric of the foregoing type has been referred to as "microvelcro" and is a product of the 3M Corp.

A pressure pad 64, which may be fabricated of plastic foam material, is adhesively secured to the pressure-sensitive adhesive portion 42 on the underside of tab 44. When the bandage 40 is in the position of FIG. 9 on a skin 65 of a patient, it will hold dressing 67 against the wound 69 which is located within the opening or window 53. It can readily be seen that tab 44 can be moved between the closed position of FIG. 9 and an open position (not shown) to remove and replace dressing 67. It will also be appreciated that the folds 50 will lie in the horizontal position shown in FIG. 9 because of the adhesion of self-adhering surfaces to each other at 70.

Figure 10:
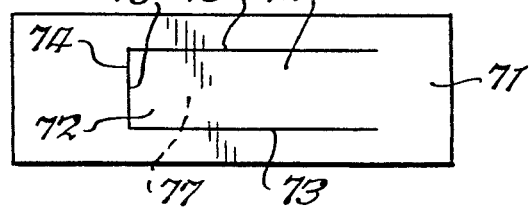
FIG. 10 is a plan view of a blank of another embodiment of the securing tape which utilizes stretchable material.
Figure 11:
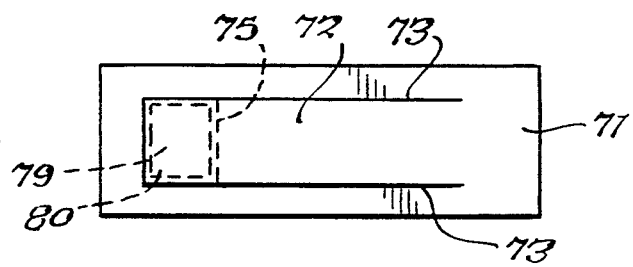
FIG. 11 is a plan view of the blank of FIG. 10 after the tab has been stretched to extend beyond the opening in the base of the tape.

In FIGS. 10 and 11 a further embodiment of the present invention is shown which utilizes a portion of the teaching of the preceding figures. In this respect, a stretchable tape 71 is provided, which may be a suitable plastic. A tab 72 is formed by cutting the tape 71 along lines 73 and 74. Thereafter, tab 72 is stretched to extend beyond the end 75 of the opening 77 which terminates at cut line 74. Hook and pile pads 79 and 80 can then be applied to the end of the tab and the base portion of the tape to maintain the tab in a closed position when required and to permit it to be selectively opened in the manner taught above relative to the preceding figures. Furthermore, it will be appreciated that the tape 71 has a pressure-sensitive surface (not shown) in the same manner as shown in the preceding embodiments.

In FIGS. 12 and 13 a modified embodiment of the present invention is shown, and its features can be incorporated into a bandage of the type shown in FIGS. 8 and 9, although it is specifically shown as a securing tape for holding a catheter or a tube. In this respect, securing tape 82 is fabricated of self-adhering fabric, as described above, having a pressure-sensitive surface 83 and a self-adhering outer surface 84. The tab 85 is an integral extension of base portion 87 in the same manner as described above relative to the embodiment of FIG. 1. The outer end 87 of tab 85 is formed in the same manner as the outer end 54 of tab 44 of FIG. 8. A handle 89 is attached to the outer end 87 in the same manner as described above relative to FIG. 8. Folds 90 have fold portions 91 and 92 superimposed on each other in the same manner described above relative to FIGS. 8 and 9, and fold 90 lies horizontally because adjacent portions are attached to each other at 96 by the self-adhering fabric. The folds 90 are formed in relatively central parts of edge portions 88 on opposite sides of tab 85.

In FIGS. 14 and 15 a still further embodiment of the present invention is shown wherein securing tape 82a is substantially identical to securing tape 82 of FIGS. 12 and 13. The only difference is that the folds 90a formed of fold portions 91a and 92a extend in the opposite direction from fold 90 of FIG. 13. Otherwise, the embodiment of FIGS. 14 and 15 is identical to the embodiment of FIGS. 12 and 13, and the numerals with the postscript b designate structure which corresponds to structure designated by like numerals without a postscript in FIGS. 12 and 13.

In FIGS. 16 and 17 a further embodiment 82b of the present invention is shown which is identical to the embodiment of FIGS. 12 and 13 except that the folds 90b formed from edge portions 88b are located proximate the outer end portion 87b of tab 85b. Folds 90b consist of fold portions 91b and 92b. Folds 90b extend in the same direction as folds 90 of FIG. 12. The numerals with a postscript b designate structure which corresponds to structure designated by like numerals without a postscript in FIGS. 12 and 13.

In FIGS. 18 and 19 a securing tape 82c is shown which is identical in all respects to securing tape 82b of FIGS. 16 and 17 except that the folds 90c are in the reverse direction of fold 90b. The numerals with a postscript c designate structure which corresponds to structure designated by like numerals without a postscript in FIGS. 12 and 13.

In FIGS. 20 and 21 a securing tape 82d is shown which is identical in all respects to the embodiment of FIGS. 12 and 13 except that folds 90d which are formed from side edge portions 88d is located substantially at the centers of the latter and serve as rests for tube 37d. Folds 90d have an upper fold portion 91d and a lower fold portion 92d. The numerals with a postscript d designate structure which corresponds to structure designated by like numerals without a postscript in FIGS. 12 and 13.

In FIGS. 22 and 23 a securing tape 82e is shown which is identical in all respects to the securing tape 82d of FIGS. 20 and 21 except that the folds 90e which consist of fold portions 91e and 92e extend in the reverse direction from folds 90d. The numerals with a postscript e designate structure which corresponds to structure designated by like numerals without a postscript in FIGS. 12 and 13.

In FIGS. 24 and 25 a securing tape 82f is shown wherein the folds 90f are located in side edge portions 88f proximate the junctions 84f of tab 85f and base portion 87f. Folds 90f include upper portions 91f and lower portions 92f. The numerals with a postscript f designate structure which corresponds to structure designated by like numerals without a postscript in FIGS. 12 and 13.

In FIGS. 26 and 27 a securing tape 82g is shown which is identical in all respects to securing tape 82f of FIGS. 24 and 25 except that folds 90g are oriented in a reverse direction from folds 90f. The numerals with a postscript g designate structure which corresponds to structure designated by like numerals without a postscript in FIGS. 12 and 13.

As noted above, all of the securing tapes shown in FIG. 12 through FIG. 27 are fabricated from self-adhering fabric having an outer surface which will stick to itself, thereby eliminating the need for hook and pile fasteners at the outer ends 87 of the tabs. It is to be again noted that while the embodiments shown in FIGS. 12 through 27 have been specifically designated as securing tapes for tubular members, the term securing tape includes bandages such as shown in FIGS. 8 and 9. More specifically, the embodiments of FIGS. 12 through 27 can have a pressure pad, such as 64 of FIG. 9, associated therewith, thus making them bandages for holding dressings, as described above relative to FIGS. 8 and 9.

Figure 28:
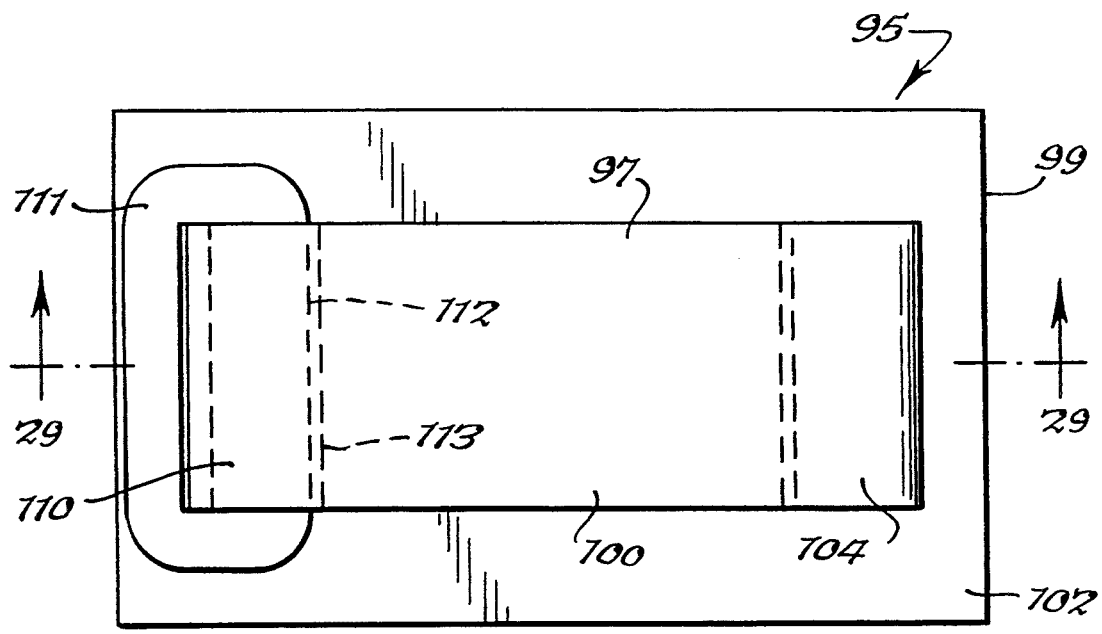
FIG. 28 is a plan view of still another embodiment of a tape which can be utilized either as a bandage or as a securing tape and which utilizes self-adhering fabric.
Figure 29:
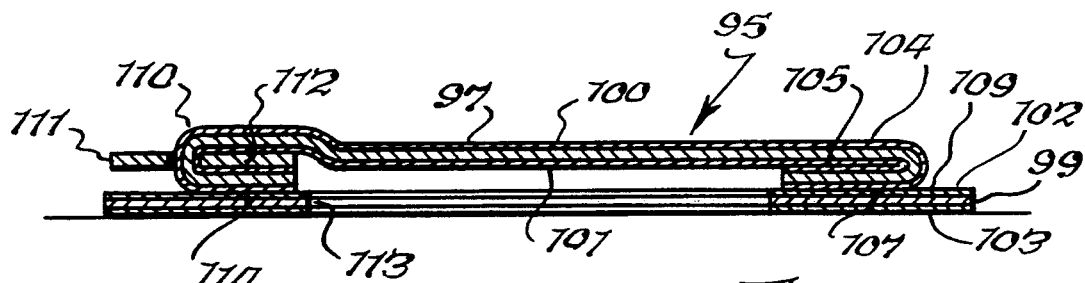
FIG. 29 is a cross sectional view taken substantially along line 29—29 of FIG. 28.

In FIGS. 28 and 29 a still further embodiment of the present invention is shown. In this embodiment a securing tape in the form of a bandage 95 is shown which is also fabricated entirely of self-adhering fabric except that the tab 97 is separate from base portion 99. Tab 97 has an outer surface 100 of self-adhering fabric and an inner surface 101 of pressure-sensitive adhesive. Base 99 has an outer surface 102 of self-adhering fabric and an inner surface 103 of pressure-sensitive adhesive. The end 104 of tab 100 is folded over on itself so that the adhesive 101 sticks to itself at 105, and the outer self-adhering surface at 107 is caused to attach itself to the outer adhering surface 109 of base 99. The free end 110 of tab 97 is folded over on itself and a handle 111 has a portion 112 adhesively secured within folded-over portion 110. An opening 113 is located in base portion 99 underlying the portion of tab 97 between folded-over portions 104 and 110. When it is desired to insert a foreign body, such as a dressing, under tab 97, it is merely necessary to grasp handle 111 to separate the self-adhering surfaces at 114, and they can be reattached after the foreign body is inserted under tab 97. Also, if desired, a second handle like 111 can also be installed at folded-over portion 104 in the same manner as at portion 110. As with the previous embodiments of FIGS. 12–27, the securing tape 95 can function either as a bandage, as shown in FIGS. 8 and 9, or as a hold-down for a tube, catheter or the like, as shown in FIG. 1.

Figure 30A:
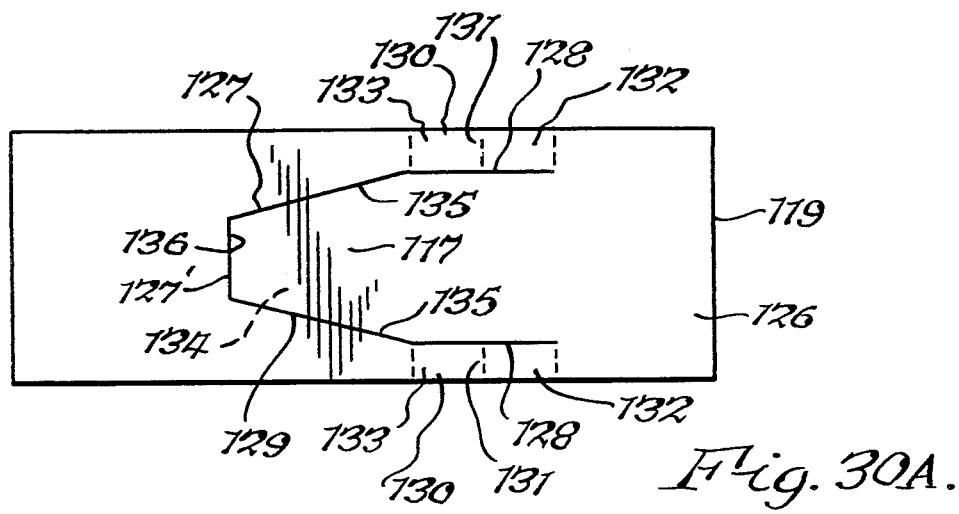
FIG. 30A is a plan view of the blank from which the embodiment of FIG. 30 is fabricated.

In FIGS. 30, 30A and 31 a securing tape 115 is shown which constitutes a further modification of the present invention. In this embodiment the tab 117 is cut out of the base 119 of the tape, which has a pressure-sensitive undersurface 120 and a nonadhering outer surface 121. The embodiment 115 is shown as a bandage having a plastic foam pressure pad 122 secured to the adhesive on the underside of tab 117 for bearing on dressing 122'. The outer end 123 of tab 117 is folded over on itself to provide a grasping portion, as described above in FIG. 1. A hook fabric 124 is adhesively secured to base 119 and a mating pile fabric 125 is secured to the adhesive on the underside of tab 117. In the embodiment of FIGS. 30 and 31, the tab 117, as noted above, is cut out of base 119 in the shape of a trapezoid having edges 127, 127' and 129, with parallel cuts 128 proximate the layer base of the trapezoid. The edge portions 130 at parallel cuts 128 from which securing tape 115 is formed are folded over at folds 131 which have upper portions 132 and lower portions 133. The edges 135 and 137 of opening 134 are also of the shape of a trapezoid so that after the folds 131 are made, the edge portions 139 of tab 117 will overlie opening 134 as shown in FIG. 30 so that the adhesive 120 on the undersurface of tab 117 will lie over portions of the base so that the tab can be adhesively secured thereto.

In FIG. 32 a cross sectional view is shown of a bandage 140 which utilizes the same blank 126 as shown in FIG. 30A and is identical in all respects except that it is fabricated out of self-adhering fabric of the type described above so that the use of the hook and pile fabric of FIGS. 30 and 31 is eliminated. In this respect, bandage 140 includes a trapezoidal tab 141 which is identical to trapezoidal tab 117 of FIG. 30. Tab 141 is an extension of base 142 and there is a fold 143, which may be identical to fold 131 of FIG. 30, on each side of tab 141. A handle 144, which is analogous to handle 111 of FIG. 28, has a portion 145 adhesively secured by the adhesive 147 on the underside of tab 141 and which is located within bent-over portion 149 at the outer end of tab 141. The free end of tab 141 is selectively attached to the base 142 at 150, where the self-adhering portions of the tab and the base are brought into contact. As in the embodiment of FIG. 30, a pressure pad 151 of suitable foam material, such as foam polyurethane, is adhesively attached to the adhesive 147 on the underside of tab 141, and, in use, it bears on a dressing 152 which is applied to a wound.

FIG. 33 is a fragmentary cross sectional view of a securing tape 115b which can be identical in all respects to the embodiments of FIGS. 30 or 32 but which is used as a hold-down for a catheter 37b. In other words, by eliminating the compression pads 122 and 151 of FIGS. 31 and 32, respectively, the bandages 115 and 140 can also be used as securing tapes for catheters or the like.

In FIGS. 34 and 35 a further embodiment is shown. FIG. 34 is a plan view of a modified form of the embodiment of FIG. 30 is shown which utilizes a substantially triangular tab 117a, rather than the trapezoidal tab 117 of FIG. 30. The folds 131a are identical to folds 131 of FIG. 30. The embodiment of FIGS. 34 and 35 does show that the adhesive undersurface 120a of base 119a will adhere to the upper surface of the bandage in areas 139a. As in FIG. 31, a pressure pad 122a is adhesively secured to the underside of tab 117a. Hook fabric 124a is adhesively secured to base 119a and pile fabric 125a is adhesively secured to the underside of tab 117a. The numerals with a postscript a designates structure which corresponds broadly to structure designated by like numerals without a postscript in FIGS. 30 and 31.

In FIG. 36 there is a fragmentary showing of a medical securing tape 115c which is identical in all respects to the embodiment of FIGS. 34 and 35 except that the pressure pad 122a has been eliminated so that the device 115a can serve as a securing tape for a catheter, such as 37b.

In FIGS. 37 and 38 a still further embodiment of the present invention is shown. The bandage 154 is fabricated from a tape having a base 155 with an undercoating of pressure-sensitive adhesive 157 throughout its length. The tab 159 is cut out of base 155 and is integrally attached thereto at 160. The tab 159 has curved sides 161 so that when a fold 162 is made, which is identical to fold 131 of FIGS. 30 and 31, the outer free end of tape 159 will extend beyond the edge 163 of opening 164 which is formed as a result of cutting the tab out of the base. Thus, there will be overlapping portions 165 wherein the adhesive 157 on the underside of base 155 can adhere to the outer surface of the base. Hook fabric 167 is adhesively secured to base 155 and pile fabric 169 is adhesively secured to the outer end of tab 159. The extreme outer end of tab 159 is turned over at 168 to provide a portion of the tab which can be grasped to open the tab and thus pull away pressure pad 170 from a dressing 171 which it may be holding against a wound. As with the embodiments of FIGS. 30, 32 and 35, if the pressure pad 170 is eliminated, the device 154 of FIGS. 37 and 38 can be used as a medical securing tape for catheters or tubes or needles.

In FIGS. 39 and 40 a still further embodiment of the present invention is disclosed. The securing tape is in the form of a bandage 173 which comprises a base 174 having a nonadhesive outer surface 175 and a pressure-sensitive adhesive undersurface 177 throughout its length which will stick to practically anything including silicone surfaces, thereby providing excellent adhesion to oily skin. A tab 179 is cut out of the base of the tape along three lines 180 and 181 to thereby produce an opening 182 underneath tab 179. The tab 179 is an integral extension of the base and is connected thereto at its inner end 183. A strip of plastic MYLAR-like material 184 is adhesively secured to the upper surface 175 at portions 185 and 187 which overlap the base. This material can have an adhesive undersurface to effect the adhesion. The portion 189 of strip 184 lies over the opening 182. In other words, portion 189 extends to the right of the end 190 of opening 182 in FIGS. 39 and 40. The extreme outer end of tab 179 is bent over on itself at 191 so as to cause the adhesive on the underside of the tab to adhere to itself at 192. The adhesive on the underside of tab 179 at 193 can adhere to the plastic MYLAR-like material 184. A pressure pad 194 of foam material, such as polyurethane, is adhesively secured to the underside of tab 179 and, in use, it bears on a dressing 195 which is applied to the person's body. When it is desired to change the dressing 195, all that is necessary is to grasp the outer end portion 191 of the tab where it is folded over and pull the adhesive at 193 away from the MYLAR-like material 184. After a new dressing has been applied, the adhesive at 193 can be reattached to the MYLAR-like material 184. There are two special features of bandage 173. The first special feature is that folds are not required to foreshorten the opening 182, as in certain of the previous embodiments. Instead, the MYLAR-like strip 184 extends over the end of the opening 182 so that the outer end of the tab can stick to it to close the bandage. In addition, there is a special relationship between the adhesive 177 and the MYLAR-like material in that the adhesive will stick repeatedly to the MYLAR-like material but it will not leave any residues of adhesive. Thus, the outer end of tab 179 can be selectively adhesively secured and separated from the MYLAR-like material 184 repeatedly. The MYLAR-like material has a very shiny or glossy outer surface like that of the 3M tape identified by number 3750G. In fact, any suitable tape having a shiny or glossy surface to which a tape having pressure-sensitive adhesive thereon which can be repeatedly applied and removed can be used. Products of the 3M Corp. which have the two parts which can selectively repeatedly be fastened and unfastened are identified by the designations MSX-1226 and MSX-1213, wherein the MSX-1226 is the combined base 174 and tab 179, and the MSX-1213 is the MYLAR-like material 184.

In FIG. 41 there is a fragmentary showing of a modification 173a of the embodiment of FIG. 39 which is used as a medical securing tape for an item such as catheter 37. In this respect, the securing tape 173a is identical in all respects to the embodiment of FIGS. 39 and 40 except that the pressure pad 194 has been eliminated so that the adhesive 177 can adhesively attach to catheter 37b to hold it in position.

In FIGS. 42 and 43 a further embodiment of the present invention is shown. The securing tape in the form of bandage 173b is formed of a piece of tape having a base 174b which is identical in all respects to base 174 of FIGS. 39 and 40. There is a tab 179b which is identical in all respects to tab 179 of FIG. 39. Also, there is an opening 182b where tab 179b is cut out of base 174b. The bandage 173b carries a pressure pad 194b which bears on a dressing 195b. However, the bandage 173b differs from the bandage 173 in that a strip of hook fabric 197 has border portions 199 and 200 which are adhesively secured to tape 174b, and the portion 201 of hook fabric 197 overlies opening 182b which terminates at edge 190b. A strip of pile fabric 202 is adhesively attached to the underside of tab 179b for selective attachment to hook fabric 197. The outer end 191b of tab 179b is bent over and adhesively secured to itself at 192b to provide a tab which can be grasped. As noted above, the embodiment of FIGS. 42 and 43 utilizes a blank which is identical to that described above in FIGS. 39 and 40. The only difference is that hook and pile fabric is utilized to attach the outer end of the tab to the base, whereas in FIG. 39 a MYLAR-like material is used in conjunction with the adhesive on the underside of the tab.

In FIG. 44 a modified embodiment of FIGS. 41 and 42 is shown. The securing tape 173c is identical in all respects to the device of FIGS. 42 and 43 except that the pressure pad 194b has been eliminated and the tab 179c is utilized to secure a catheter 37b. Thus, the securing tape of FIG. 44 is for holding an item, such as a tube or catheter, as contrasted to the securing tape of FIGS. 42 and 43 which is a bandage for holding a dressing.

In FIGS. 45 and 46 a still further embodiment of the present invention is disclosed. A bandage 173d includes a base 174d which is identical in all respects to base 174 of FIGS. 39 and 40 and it includes a tab 179d which has edges 180d and 181d. A C-shaped piece of MYLAR-like material 187d includes portions 205 and 207. Portions 205 include portions 209 which are adhesively secured to base 174d and portions 210 which overlie the opening 182d. The end portion 207 of the C-shaped MYLAR-like material includes a portion 211 which is adhesively secured to base 174d and a portion 212 which extends inwardly over opening 182d from the edge 190d of the opening. The outer end 191d of tab 179d is bent over on itself so that the adhesive 177d can adhere to itself at 192d and thus provide a portion which can be grasped. The adhesive at 193d can thus selectively adhere to the portion 212 of the MYLAR-like material. In addition, the adhesive on the undersurface of tab 179d can adhere to portions 210 and 212 of the C-shaped MYLAR-like material 187d. Thus, tab 179d can be secured to the base member 174d on its three free sides thereof, namely, the sides proximate edges 180d and 181d. A pad 194d is adhesively secured to the underside of pad 179d for pressing against a dressing 195d.

In FIG. 47 a modification of the embodiment of FIGS. 45 and 46 is shown. The embodiment 173e is identical in all respects to the embodiment of FIGS. 45 and 46 except that the pressure pad 194d has been eliminated so that the tab 179e can be used as a securing tape for an item such as catheter 37b. The advantage of the embodiment of FIG. 47 is that certain edge portions of tab 179e which are adjacent to its longitudinal sides can adhesively secure to the portions 210 of the C-shaped MYLAR-like member 207.

In FIG. 48 a bandage 179f is shown which is identical in all respects to the embodiment of FIGS. 45 and 46. The only difference is that a C-shaped piece of hook fabric 207f, which is identical in shape to the MYLAR-like C-shaped material 207, is attached to base 174f and a U-shaped piece of pile fabric 214 is attached to the underside of the outer edge of tab 179f for mating engagement with the portions of C-shaped hook fabric 207f which it overlies. In other words, the blank of the embodiment of FIG. 48 is identical to the blank of the embodiment of FIG. 45 and thus the base and the tab are identical. The only difference is that the hook fabric 207f is of the same C-shape as the MYLAR-like material 207 of FIG. 45, and a C-shaped pile fabric is secured on the undersides of the edges of tab 179f for mating engagement with portions of the hook fabric which are analogous to portions 210 and 212 of FIG. 45.

In FIGS. 49 and 50 a still further embodiment of the present invention is shown. The bandage 217 is fabricated from a piece of tape 219 having a plain upper surface 220 and a pressure-sensitive adhesive undersurface 221. The bandage 217 includes a base 222 with a tab 223 which is cut therefrom along lines 224 and 225, with the three lines defining the size of opening 227. The end 230 of tab 223 is an integral portion of tape 219. A handle 231 has a slot 232 therein through which the end portion 233 of tab 223 is threaded and the adhesive 221 fastens handle portion 234 to the outer end of tab 223. Handle 231 has a portion 235 which protrudes beyond tab 223. Pile fabric material 237 is adhesively secured to the underside of handle portion 235. A mating piece of hook fabric material 239 is adhesively secured to base portion 222 and overlies opening 227. Handle portion 235 extends beyond the end 225 of opening 227, and the hook and pile fabric materials 239, 237 can secure the outer end of tab 223 to base portion 222. To complete the bandage, a foam pad 240 is adhesively secured to the underside of tab 223 for bearing against a dressing 241 which is applied to a wound. It can readily be seen that the hook and pile fasteners 239, 237 can be selectively detached and attached during the process of replacing dressings 241.

In FIG. 50A a modification of the embodiment of FIG. 49 is shown. In this embodiment the hook fabric 239a is secured to the portion of the base beyond opening 227a, and handle 231a is longer than handle 231 of FIG. 49 and carries pile fabric 237a so that it can mesh with pile fabric 239a. By causing the hook fabric to be located beyond opening 227a, a larger amount of opening 227a can be utilized for a dressing in the sense that a pad such as 240a and a dressing such as 241a can extend beyond the end of the tab and underneath the handle 231a. The numerals with a postscript a of FIG. 50A correspond to numerals without this postscript of FIGS. 49 and 50.

In FIG. 51 a modification 217a of securing tape 217 of FIGS. 49 and 50 is shown. This modification constitutes a securing tape 217a which is identical in all respects to the embodiment of FIG. 49 and which includes a tab 223a but does not include the pressure pad 240. Thus, the securing tape 217a can be used for securing a catheter, such as 37b, to a foreign object.

In FIGS. 52-55 a still further embodiment of the present invention is shown. This embodiment is somewhat similar to the embodiment of FIG. 1 except that the folds are in a different position. The medical securing tape 245 is formed of ordinary tape material having a nonadhesive outer surface 247 and a pressure-sensitive adhesive undersurface 249. A tab 250 is cut out of base 251 along lines 252 and 253 which simultaneously creates opening 254. The end portion 255 of tab 250 is integrally attached to base portion 251. In order to cause the outer end 257 of the tab 250 to extend beyond the end 253 of opening 254, folds 259 are made as shown by causing the portions 260 of the base 251 lying to the right of the extreme end 255 of tab 250 to overlie the longitudinal edge portions 261 which are folded under portions 260 at 262. Thus, the opening 254 will extend between end 253 and end 263 (FIG. 52), and the side edges of opening 254 will be along lines 264. In order to secure the outer end 257 of tab 250 to base portion 247, hook fabric 265 is adhesively secured to base portion 247 and pile fabric 267 is secured to the underside of tab 250. The end 257 of tab 250 is bent over so that the adhesive portions at 269 attach to each other to provide an end which can be grasped when it is desired to separate the hook and pile fastening members. In the embodiment 245, the tab 250 pivots about line 263 along with folds 259 which also pivot around line 263. In this embodiment the folds 259 should not be fastened to the remainder of the base member. In this respect, in FIG. 55 there is a fragmentary showing of the tab 250 and folds 260 in a raised position.

Figure 56:
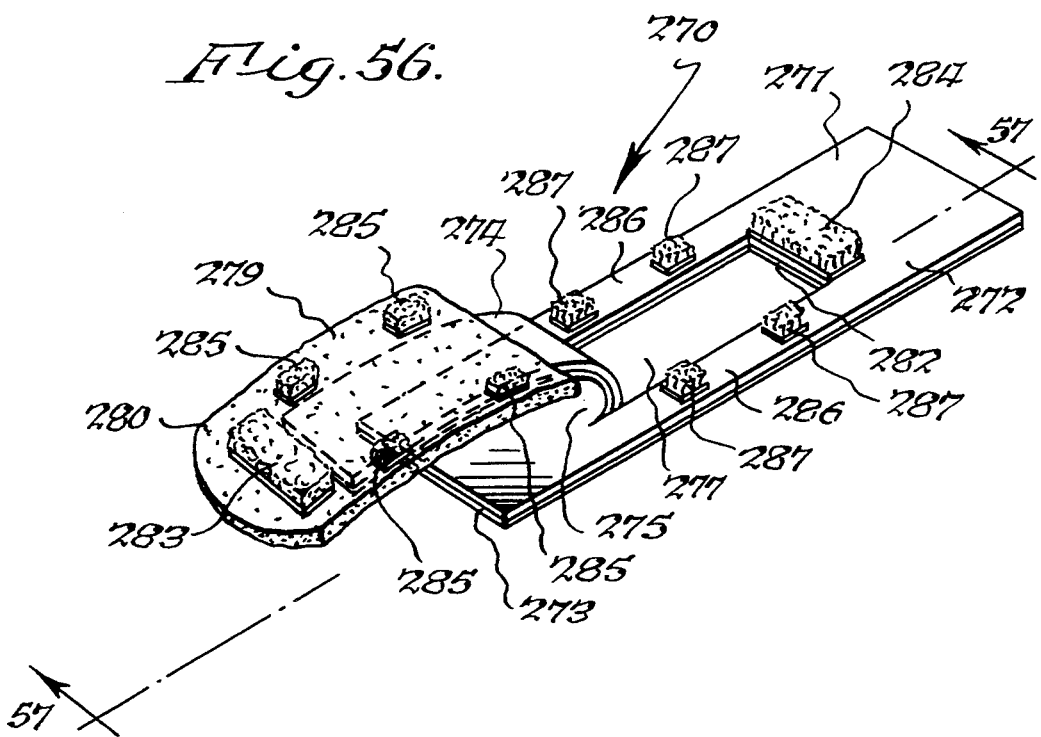
FIG. 56 is a perspective view of another embodiment of the present invention relating to a bandage with the tab in an open position.
Figure 57:
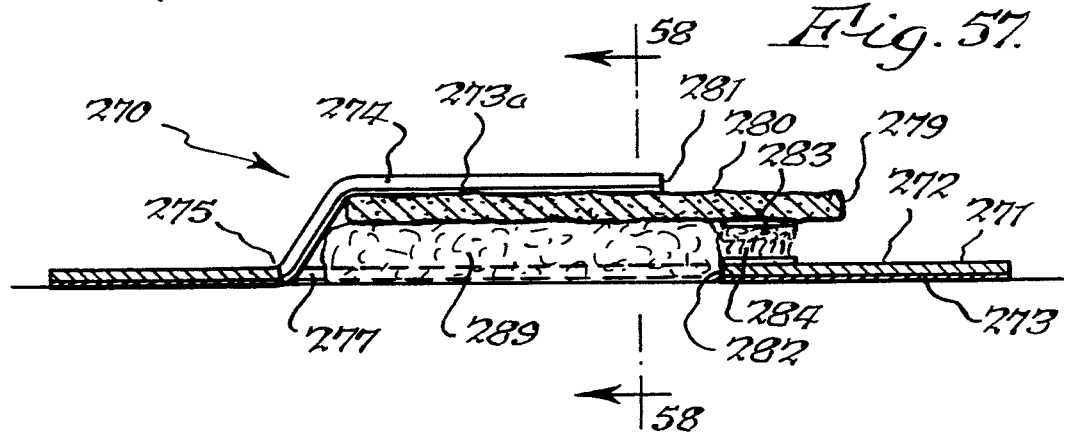
FIG. 57 is a cross sectional view taken substantially along line 57—57 of FIG. 56 with the tab in a closed position holding a dressing in place.
Figure 58:
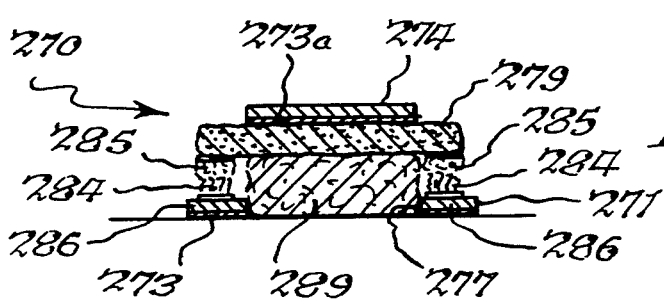
FIG. 58 is a cross sectional view taken substantially along line 58—58 of FIG. 57.
Figure 65:
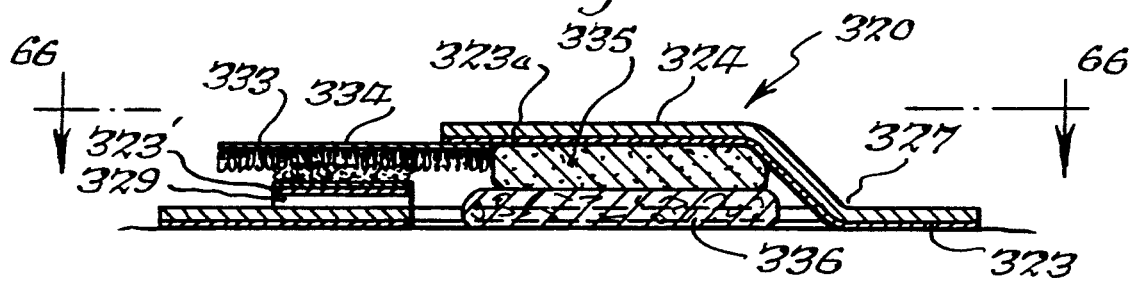
FIG. 65 is a cross sectional view of still another embodiment of the present invention taken substantially along line 65—65 of FIG. 66.
Figure 66:
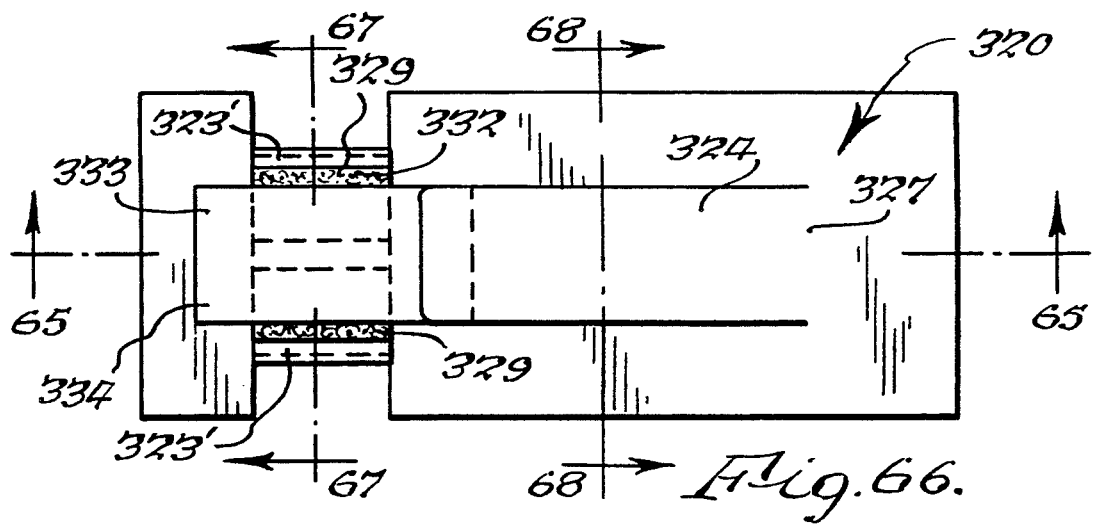
FIG. 66 is a plan view of the embodiment of FIG. 65 taken substantially in the direction of arrows 66—66 of FIG. 65.
Figure 67:
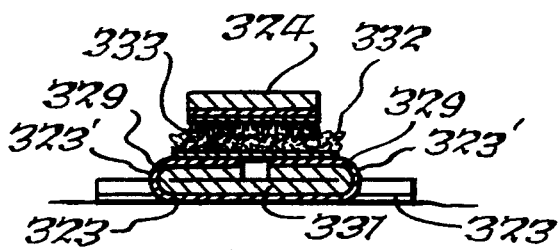
FIG. 67 is a cross sectional view taken substantially along line 67—67 of FIG. 66.
Figure 68:
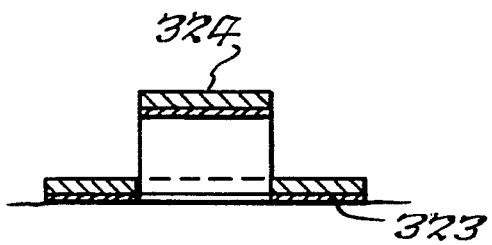
FIG. 68 is a cross sectional view taken substantially along line 68—68 of FIG. 66.
Figure 69:
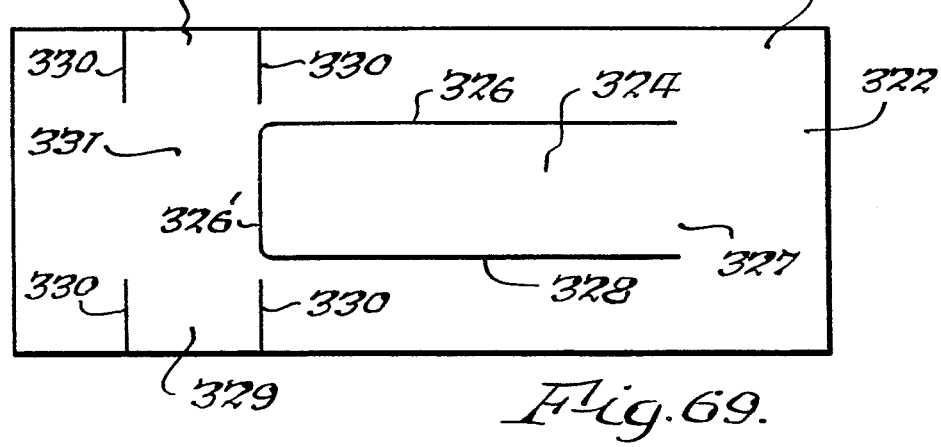
FIG. 69 is a plan view of the blank utilized to make the embodiment of FIG. 65.

In FIGS. 56, 57 and 58 a still further embodiment of a securing tape 270 in the form of a bandage is shown. Securing tape 270 includes a base portion 271 of tape having an outer surface 272 and a pressure-sensitive adhesive undersurface 273. A tab 274 is formed integrally with base portion 271 and is attached thereto at 275. An opening 277 is located where tab 274 was cut out. A pressure pad 279 is adhesively secured to the pressure-sensitive adhesive portion 273a on the underside of tab 274. Pressure pad 279 is fabricated of suitable foam plastic material, but it can be fabricated of any other suitable material which will provide a pad function. The portion 280 of pressure pad 279 extends outwardly beyond the end 281 of tab 274 an amount which will cause it to overlie the part of base portion 271 beyond the end 282 of opening 277 so that pile fabric 283 which is adhesively secured to pad portion 280 can be engaged with hook fabric 284 which is adhesively secured to the base portion 271 of the securing tape. The pressure pad 279 is wider than opening 277 so that it overlies portions of strips 286 of the base portion 271 on opposite sides of opening 277. Pile fabric sections 285 are adhesively secured to pressure pad 279 and they engage hook fabric sections 287 which are adhesively secured to strips 286. Thus, when the tab 274 and pressure pad 279 are in the closed position of FIG. 57, pad 279 will not only bear on dressing 289, but the mating fabric portions 285, 287 and 283, 284 will substantially completely enclose dressing 289.

Thus, the embodiment of FIGS. 56-58 performs a plurality of functions, namely, (1) the pressure pad 279 constitutes an extension of tab 274 so that the tab 274 can essentially be elongated beyond opening 277 so that it can be fastened to the base portion at the opposite end of the opening from the area 275 at which it is connected to the base portion, and (2) the pressure pad 279 is wider than opening 277 so that the sides of the pressure can be attached to the base portion strips 286. Furthermore, it will be appreciated that, if desired, the hook and pile fabric of FIG. 56 need not be configured in sections as shown, but each can be configured essentially in the shape of a U so that there is complete sealing along the sides of opening 277, rather than the intermittent sealing as shown. Additionally, while hook and pile fabric has been depicted as the arrangement for securing the tab to the base portion, it will be appreciated that MYLAR-like film, such as shown and described relative to FIG. 40, can be utilized on the base portion 271, and a suitable adhesive can be applied to the underside of pressure pad 279 to coact therewith in the manner described above relative to FIG. 40. In addition to the foregoing, it will be appreciated that the bandage 270 can be used to hold down a tube which enters a wound, with the tube passing through the space between the two pieces of hook fabric 287 on one of the strips 286.

In the preceding description references have been made to tape which has an outer surface which does not stick to itself and to a pressure-sensitive adhesive thereon. Tape of this type is known under the trademark DUROPORE.

In FIGS. 59-64 a further embodiment is shown. The securing tape 300 of FIGS. 59-64 differs from the previous embodiments in that the hook fabric which is being used does not have an adhesive backing and thus is much less expensive than hook fabric with an adhesive backing, thereby decreasing the cost of the entire securing tape. The securing tape 300 is fabricated from a blank tape 301 (FIG. 63) having a nonadhesive surface 302 and a surface 303 of pressure-sensitive adhesive. A tab 304 is cut out of the base member 305 along lines 306, 307 and 308 (FIG. 63) leaving the end of the tab attached at 309. It will be appreciated that there is a layer of adhesive 310 on the underside of tab 304. A piece of hook fabric 311 which has a nonadhesive surface 312 is secured to the outer end of tab 304 by the use of the adhesive 310 on the underside thereof. Pile fabric 313 is secured by its adhesive backing 314 to the outer end portion 315 of base member 305. It can thus be seen that in this embodiment hook fabric 311 without an adhesive backing can be secured to the outer end 317 of tab 304 by the utilization of the layer of pressure-sensitive adhesive 310 at the outer end of the tab. It will be appreciated that the positions of the hook fabric and the pile fabric can be reversed, in which event the hook fabric can have an adhesive backing and the pile fabric will have a nonadhesive backing.

In FIGS. 65–69 a still further embodiment of the present invention is disclosed. This embodiment differs from the embodiment of FIGS. 59–64 in that it utilizes both hook fabric with a nonadhesive backing and pile fabric with a nonadhesive backing by taking advantage of the pressure-sensitive backing on the tape itself. The embodiment 320 is fabricated from a blank 321 (FIG. 68) which has a nonadhesive surface 322 and a layer of pressure-sensitive adhesive 323 throughout its entire undersurface. A tab 324 is cut out from the tape along lines 326, 326' and 328 leaving one end of tab 324 secured to the base member at 327. Also tabs 329 are formed by making cuts 330 leaving a portion 331 of the base member therebetween. The adhesive undersurfaces 323 on tabs 329 are brought over to the top of the securing tape 320 by bending them to the position shown in FIG. 67, and the nonadhesive surface of a piece of pile fabric 332 is secured to the adhesive portions 323' on tabs 329. Additionally, a piece of hook pile fabric 333 having a nonadhesive backing 334 is secured to the adhesive 323a on the underside of the outer end of tab 324. Thus securing tape 320 utilizes both hook fabric without an adhesive backing and pile fabric without an adhesive backing by taking advantage of the adhesive backing on the tape itself, thereby greatly reducing the cost of the securing tape over that which uses hook fabric and pile fabric with adhesive backings. It will be appreciated that the positions of the hook fabric and the pile fabric can be reversed.

In securing tape 320, a pressure pad 335 is adhered to the portion of the pressure-sensitive tape on the underside of tab 324 for holding a bandage 336 in position. However, it will be appreciated that the securing tape 320 without the pressure pad 335 can be utilized for the purpose of holding down a tubular member Such as 316 of FIG. 59 or for holding a catheter in place as described above relative to any of the preceding embodiments.

Figure 7A:
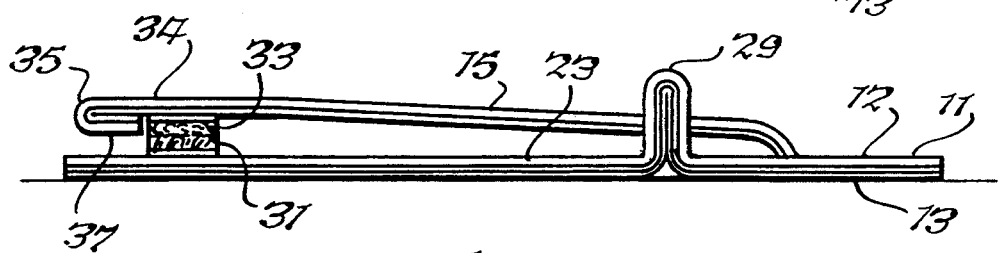
FIG. 7A is a fragmentary side elevational view of the attitude of the fold when the tape is not of the self-adhering type or when it is not flattened down as shown in FIG. 1.
Figure 70:
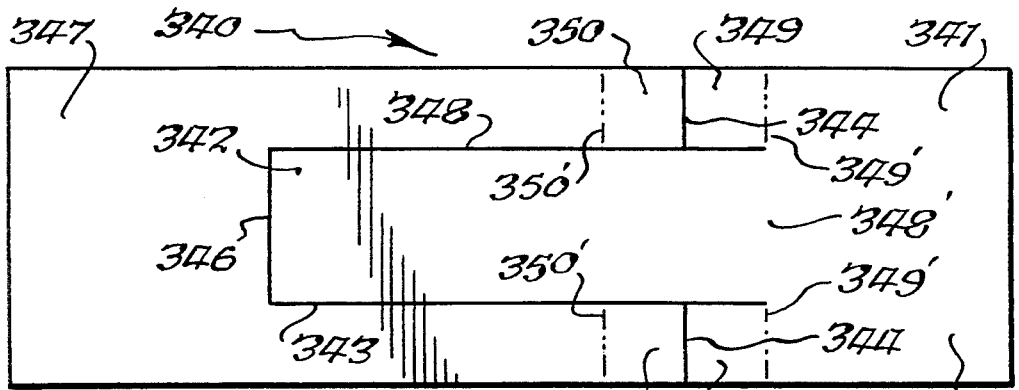
FIG. 70 is a plan view of the blank of still another embodiment of the present invention.
Figures 71, 75:
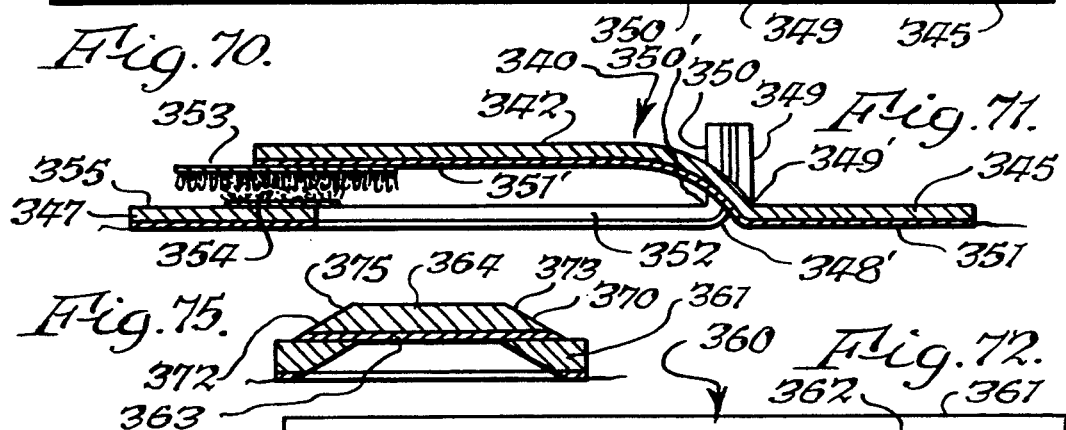
FIG. 71 is a cross sectional view taken substantially along line 71—71 of FIG. 71A of the securing tape made from the blank of FIG. 70 after it has been completely fabricated.
FIG. 75 is a cross sectional view taken substantially along line 75—75 of FIG. 74.
Figure 72:
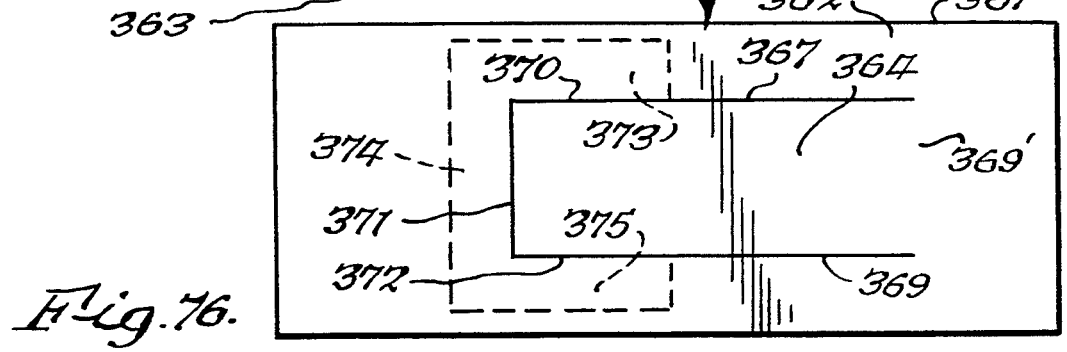
FIG. 72 is a plan view of the blank utilized to make still another embodiment shown in FIG. 73.

In FIGS. 70, 71 and 71A a still further embodiment of the present invention is disclosed. This embodiment is similar to that of FIGS. 7A and 53. However, it is easier to fabricate, as will become apparent hereafter. The blank of securing tape 340 is shown at 341. A tab 342 is cut from blank 341 by cutting it out at lines 343, 346 and 348, leaving one end of the tab secured at 348'. In addition, the blank is cut at lines 344 to provide two separate parts 345 and 347. Thereafter, part 345 will have tabs 349 and part 347 will have tabs 350. As noted above relative to the other embodiments, the entire undersurface of blank 341 has a coating of pressure-sensitive adhesive 351 thereon. Thereafter, each tab 349 is secured to its adjacent tab 350 by their adhesive undersurfaces, as shown in FIGS. 71 and 71A, to thereby foreshorten the opening 352 which is located where tab 342 was cut out. In this respect, tabs 349 are folded along lines 349' and tabs 350 are folded along lines 350', and each tab 349 is secured to its adjacent tab 350 in face-to-face relationship. Thereafter, hook fabric 353, which may have a nonadhesive backing, is secured to the adhesive 351' on the underside of tab 342. Also, pile fabric 354 which has an adhesive backing is adhesively secured to the end portion 355 of the base member of the tape. The reason that the tabs 349 and 350 are secured to each other as shown in FIG. 71, rather than making a fold, as in FIG. 7A, is because from a manufacturing viewpoint it is much simpler to do that which is shown in FIGS. 70, 71 and 71A than to make a fold.

Figure 74:
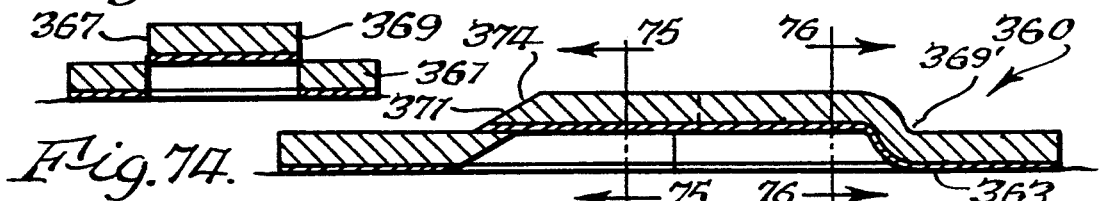
FIG. 74 is a cross sectional view taken substantially along line 74—74 of FIG. 73.
Figure 73:
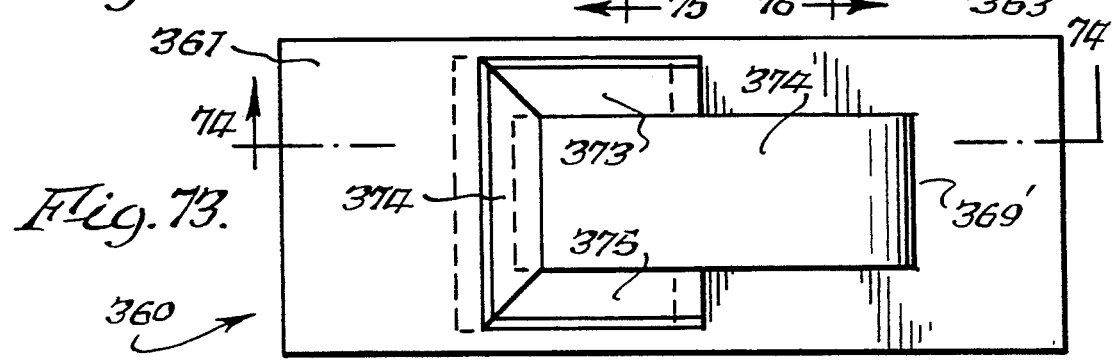
FIG. 73 is a plan view of the embodiment made from the blank of FIG. 72.

In FIGS. 72–76 a still further embodiment of the present invention is disclosed. In this embodiment external fastening arrangements need not be used in view of the manner in which the securing tape is cut. The securing tape 360 is fabricated from tape blank 361 having an upper surface 362 and an undersurface with a layer 363 of pressure-sensitive adhesive thereon. The tab 364 is cut from base member 365 in the following manner. Cuts 367 and 369 are perpendicular to the surface of the tape (FIG. 76). Cuts 370, 371 and 372 are cut at an angle as shown in FIGS. 74 and 75 so as to produce portions 373, 374 and 375, respectively, which, when placed in overlying relationship to the adjacent portions of upper surface 62, will provide an overlap so as to fasten the tab 374 to the upper surface of the base because the adhesive on the undersurfaces of portions 373, 374 and 375 will thus adhere to the base member. Tab 364 is attached to the base member 365 at 369'. It will be appreciated that the system used relative to FIGS. 71–76 is limited to the use with tapes having a sufficient thickness.

In FIGS. 77–79 a securing tape 380 is shown which is a modification of the embodiments of FIGS. 70, 71 and 71A. In this embodiment the two separate parts 345 and 347 are joined by lapping tabs 349 and 350 rather than joining them in face-to-face relationship as shown in FIGS. 71 and 71A. Otherwise, all parts are the same. The advantage of the embodiment of FIGS. 77–79 is that the outer surface of the securing tape 380 is flatter than that of FIGS. 71 and 71A.

In FIGS. 80–82 a still further embodiment of the present invention is shown. The securing tape 382 provides a cross-over holddown for a body such as tube 383. In this embodiment a tape 384 has tabs 385 and 387 cut out from the base 389 which has a pressure-sensitive undersurface 390 throughout which includes both the base portion and the tabs. Tab 385 is secured to and integral with base portion 389 at 391, and tab 387 is secured to and integral with base portion 389 at 392. Hook fabrics 393 and 394, which do not have an adhesive backing, are secured by the adhesive 390 to the outer ends of the undersides of tabs 385 and 387, respectively. Pile fabrics 395 and 397, which have adhesive backings, are secured to base portion 389 as shown. It can thus be seen that tabs 385 and 387 cross over tube 383 from opposite directions and the adhesive undersurfaces on the tabs hold it in position in this manner. It is to be noted that the space S between the points 391 and 392 at which tabs 385 and 387, respectively, are joined to base portion 389 is wider than the diameter of tube 383, which provides a latitude for placement of tube 383 between areas 391 and 92 after base 389 has been secured to a foreign body, such as a patient. The embodiment of FIGS. 80–82 is in part related to the embodiments of FIGS. 59 and 71 in that it utilizes hook fabric which does not have an adhesive backing. The nonadhesive sides of the hook fabric do not have to be covered. Furthermore, the ends of the hook fabrics 393 and 394 extend beyond the pile fabrics 395 and 397, respectively, to facilitate the grasping of the outer ends of the hook fabrics for detaching them from the pile fabrics.

In FIGS. 83–85 a securing tape 400 is shown which is a modification of the securing tape 382 of FIGS. 80–82. As in the other embodiments the entire undersurface of blank 407 has a coating 409 of pressure-sensitive adhesive thereon which includes the undersurfaces of tabs 403 and 404. The only difference between the embodiments of FIGS. 80–82 and FIGS. 83–85 is that the areas 401 and 402 at which tabs 403 and 404, respectively, are joined to base portion 405 of tape 407 are closer together than the areas 391 and 392 of the embodiment of FIGS. 80–82. In this respect, the areas 401 and 402 at which tabs 403 and 404, respectively, of FIGS. 83–85 are joined to the base portion 405 are practically in line with each other (FIG. 83), and thus each of tabs 403 and 404 will wrap around tube 410 as depicted in FIGS. 84 and 85 to thereby hold it very securely against movement. As with the embodiment of FIGS. 80–82, the outer ends of tabs 403 and 404 have hook fabric 411 and 412, respectively, secured to the outer ends thereof by the adhesive on the undersurfaces of these tabs, considering that hook fabrics 411 and 412 do not have an adhesive backing. Pile fabrics 413 and 414, which have adhesive backings, are secured to the base portion 405. The outer ends of the hook fabrics 411 and 412 extend beyond the pile fabrics 413 and 414, respectively.

In FIGS. 86–88 a further securing tape 415 is shown which is a modification of the embodiments of FIGS. 80 and 83. This embodiment includes tabs 417 and 419. Tab 417 is joined to base portion 420 at 421, and tab 419 is joined to tab 417 at area 422. The entire blank 423 including tabs 417 and 419 has a pressure-sensitive coating of adhesive 424 on its entire undersurface. Thus, as in the embodiments of FIGS. 80 and 83, the hook fabric 425, which does not have an adhesive surface, is secured to the outer end of tab 417 by the adhesive undersurface 424 on the outer end thereof, and hook fabric 427, which does not have an adhesive surface, is secured to the outer end of tab 419 by the adhesive undersurface 424 on the outer end thereof. Pile fabrics 429 and 430, which do have adhesive backings, are secured thereby to the upper surface of base 420 as shown. The embodiment of FIGS. 86–88, in addition to having a tab-on-tab construction, also constitutes a combination of the embodiments of FIGS. 80 and 83 in that the tab 417 partially encircles tube 431 as in FIG. 83 and the other tab 419 merely crosses over tube 431. The embodiment of FIGS. 86–88 differs from those of FIGS. 80 and 83 in that the wider tab 417 has two spaced portions 417a and 417b which grip tube 431 in addition to the grip provided by tab 419. As in the embodiments of FIGS. 80 and 83, the adhesive undersurfaces of the tabs hold tube 431 in position. Also, as in the embodiments of FIGS. 80 and 83, the hook fabrics do not have adhesive backings.

It will be appreciated, however, that the crossover holddown embodiments of FIGS. 80–88 which utilize two tabs need not be restricted to the use of hook or pile fabric without adhesive backing for securing the tabs to the base portion, but they can utilize any of the securing means set forth in any of the preceding embodiments which are not inconsistent therewith.

It will also be appreciated that various features disclosed in certain embodiments can be incorporated in other embodiments, even though no specific mention has been made to this effect. Accordingly, it will be appreciated that such incorporation is within the scope of this disclosure unless such incorporation is inconsistent with the structure itself.

While preferred embodiments of the present invention have been disclosed, it will be, appreciated that it is not limited thereto but may be otherwise embodied within the scope of the following claims.

What is claimed is:

1. A securing tape for securement to a foreign body comprising an elongated tape including a base portion and a tab, said base portion and said tab each having first and second sides, said first side of said base portion and said first side of said tab being continuations of each other, an adhesive layer on said first side of said tape, said adhesive layer being on said first side of said base portion for securing said base portion to a foreign body, said adhesive layer also being on said first side of said tab, said tab having a fixed end and a free end, said tab being formed by cutting it out of said tape while leaving said fixed end integrally attached to said base portion, an opening in said base portion, said opening being formed in the location from which said tab was cut out of said tape, an outer end on said opening remote from said fixed end of said tab, a piece of one of hook fabric or pile fabric having a nonadhesive back and the other piece having an adhesive back, first and second portions on said piece of hook fabric or pile fabric, said first portion of said piece of hook fabric or pile fabric having its nonadhesive back adhesively secured to said adhesive layer at said free end of said tab, said second portion of said piece of hook fabric or pile fabric extending outwardly beyond said free end of said tab, and the other of said piece of hook fabric or pile fabric having an adhesive back secured to said second side of said base proximate said outer end of said opening for receiving in mating relationship said outer portion of said piece of hook fabric or pile fabric secured to said tab.

2. A securing tape as set forth in claim 1 wherein said one of said piece of hook fabric or pile fabric secured to said free end of said tab also extends beyond said other of said piece of hook fabric or pile fabric secured to said second side of said base.

3. A securing tape as set forth in claim 1 including a second tab, said second tab having first and second sides with said adhesive layer being on said first side of said second tab, said second tab having a fixed end and a free end, said second tab being formed by cutting it out of said tape while leaving its fixed end integrally attached to said base portion, a second opening in said base portion, said second opening being formed in the location from which said second tab was cut out of said tape, an outer end on said second opening remote from said fixed end of said second tab, a second piece of hook fabric or a second piece of pile fabric having a nonadhesive back, first and second portions on said second piece of hook fabric or said second piece of pile fabric, said first portion of said second piece of hook fabric or said second piece of pile fabric having its nonadhesive back secured to said adhesive layer on said free end of said second tab, said second portion of said second piece of hook fabric or said second piece of pile fabric extending outwardly beyond said free end of said tab, and the other of said second piece of hook fabric or said second piece of pile fabric secured to said second side of said base proximate said outer end of said second opening for receiving in mating relationship said outer portion of said second piece of hook fabric or said second piece of pile fabric secured to said tab.

4. A securing tape as set forth in claim 3 wherein said one of said piece of hook fabric or pile fabric secured to said free end of said tab also extends beyond said other of said piece of hook fabric or pile fabric secured to said second side of said base.

5. A securing tape as set forth in claim 4 wherein said one of said second piece of hook fabric or said second piece of pile fabric secured to said free end of said second tab also extends beyond said other of said second piece of hook fabric or said second piece of pile fabric secured to said second side of said base.

6. A securing tape as set forth in claim 3 wherein said tab and said second tab extend outwardly in opposite directions from said base.

7. A securing tape as set forth in claim 6 wherein said tab and said second tab are spaced apart from each other.

8. A securing tape as set forth in claim 3 wherein said fixed end of said tab and said fixed end of said second tab are sufficiently far apart so that said tab and said second tab extend substantially only over the top of an article which is secured by said tabs.

9. A securing tape as set forth in claim 3 wherein said fixed end of said tab and said fixed end of said second tab are sufficiently close to each other so that said tab and said second tab curl around an article which is secured by said tab and said second tab.

10. A securing tape as set forth in claim 1 including a second tab having a free end and a fixed end with said fixed end of said second tab being integrally attached to said tab, said second tab extending away from its fixed end in a direction which is opposite to the direction in which said tab extends away from its fixed end.

11. A securing tape as set forth in claim 10 wherein said tab includes a portion which curls around a portion of an article which is secured by said tab and said second tab.

12. A securing tape as set forth in claim 10 wherein said tab comprises two spaced portions on opposite sides of said second tab.

13. A securing tape for securement to a foreign body comprising an elongated tape including a base portion and a tab, said base portion and said tab each having first and second sides, said first side of said base portion and said first side of said tab being continuations of each other, an adhesive layer on said first side of said tape, said adhesive layer being on said first side of said base portion for securing said base portion to a foreign body, said adhesive layer also being on said first side of said tab, said tab having a fixed end and a free end, said tab being formed by cutting it out of said tape while leaving said fixed end integrally attached to said base portion, an opening in said base portion, said opening being formed in the location from which said tab was cut out of said tape, an outer end on said opening remote from said fixed end of said tab, a piece of one of hook fabric or pile fabric having a nonadhesive back, said piece of hook fabric or pile fabric having its nonadhesive back adhesively secured to said adhesive layer at said free end of said tab, and the other of said piece of hook fabric or pile fabric secured to said base proximate said outer end of said opening for receiving in mating relationship said piece of hook fabric or pile fabric secured to said tab.

14. A securing tape as set forth in claim 13 wherein said one of said hook fabric or said pile fabric is secured to said free end of said tab extending beyond said other of said hook fabric or said pile fabric secured to said base.

15. A securing tape as set forth in claim 13 wherein said other of said piece of hook fabric or pile fabric is secured to said second side of said base.

16. A securing tape for securement to a foreign body comprising an elongated tape including a base portion and first tab means, said base portion and said first tab means each having first and second sides, said first side of said base portion and said first side of said first tab means being continuations of each other, an adhesive layer on said first side of said tape, said adhesive layer being on said first side of said base portion for securing said base portion to a foreign body, said adhesive layer also being on said first side of said first tab means, said first tab means having a fixed end and a free end, said first tab means being formed by cutting it out of said tape while leaving said fixed end integrally attached to said base portion, an opening in said base portion, said opening being formed in the location from which said first tab means was cut out of said tape, an outer end on said opening remote from said fixed end of said first tab means, hook fabric having a nonadhesive back, pile fabric having a nonadhesive back, second tab means cut from said base member proximate said free end of said first tab means and folded over so that the adhesive layer thereof is located proximate said second side of said tape, one of said hook fabric or said pile fabric being secured to said free end of said first tab means utilizing said adhesive layer on said first tab means secured to said nonadhesive back of said hook fabric or said pile fabric, and the other of said hook fabric or said pile fabric having its nonadhesive back secured to said adhesive layer of said second tab means.

17. A securing tape for securement to a foreign body comprising an elongated tape including a base portion and first tab means, said base portion and said first tab means each having first and second sides, said first side of said base portion and said first side of said first tab means being continuations of each other, an adhesive layer on said first side of said tape, said adhesive layer being on said first side of said base portion for securing said base portion to a foreign body, said adhesive layer also being on said first side of said first tab means, said first tab means having a fixed end and a free end, said first tab means being formed by cutting it out of said tape while leaving said fixed end integrally attached to said base portion, an opening in said base portion, said opening being formed in the location from which said first tab means was cut out of said tape, an outer end on said opening remote from said fixed end of said first tab means, said base portion being cut into first and second base sections proximate said fixed end of said first tab means, second tab means formed on said first base section on opposite sides of said first tab means, third tab means formed on said second base section on opposite sides of said first tab means proximate said fixed end of said first tab means, said adhesive layer also being on said second and third tab means, said second and third tab means being secured to each other to thereby foreshorten said opening, and securing means on said free end of said first tab means and said base portion adjacent thereto for securing said free end of said first tab means to said base portion.

18. A securing tape as set forth in claim 17 wherein said second and third tab means are secured to each other in face-to-face relationship by their adhesive layers.

19. A securing tape as set forth in claim 17 wherein said second and third tab means are secured to each other in lapped relationship.

20. A securing tape for securement to a foreign body comprising an elongated tape including a base portion and a tab, said base portion and said tab each having first and second sides, said first side of said base portion and said first side of said tab being continuations of each other, an adhesive layer on said first side of said tape, said adhesive layer being on said first side of said base portion for securing said base portion to a foreign body, said adhesive layer also being on said first side of said tab, said tab having a fixed end and a free end, said tab being formed by cutting it out of said tape while leaving said fixed end integrally attached to said base portion, an opening in said base portion, said opening being formed in the location from which said tab was cut out of said tape, an outer end on said opening remote from said fixed end of said tab, a portion of said free end of said tab being formed by cuts from said base portion which are at angles which extend outwardly from said second side thereof toward said first side thereof so as to cause said first side of said tab proximate said cuts to extend beyond said second side of said tape when said tab is lifted out of said opening so that said adhesive layer on said first side proximate said cuts can adhere to said second side of said base portion adjacent thereto.

21. A securing tape for securement to a foreign body comprising an elongated tape including a base portion and a first tab, said base portion and said first tab each having first and second sides, said first side of said base portion and said first side of said first tab being continuations of each other, an adhesive layer on said first side of said tape, said adhesive layer being on said first side of said base portion for securing said base portion to a foreign body, said adhesive layer also being on said first side of said first tab, said first tab having a fixed end and a free end, said first tab being formed by cutting it out of said tape while leaving said fixed end integrally attached to said base portion, an opening in said base portion, said opening being formed in the location from which said first tab was cut out of said tape, an outer end on said opening remote from said fixed end of said first tab, a second tab, said second tab having first and second sides with said adhesive layer being on said first side of said second tab, said second tab having a fixed end and a free end, said second tab being formed by cutting it out of said tape while leaving its fixed end integrally attached thereto, a second opening in said base portion, said second opening being formed in the location from which said second tab was cut out of said tape, an outer end on said second opening remote from said fixed end of said second tab, and securing means proximate said free ends of said first and second tabs for securing said first and second tabs proximate said outer ends of said first and second openings, respectively.

22. A securing tape as set forth in claim 21 wherein said first and second tabs extend in opposite directions from said base.

23. A securing tape as set forth in claim 22 wherein said fixed ends of said first and second tabs are sufficiently far apart so that said first and second tabs extend substantially only over the top of an article which is secured by said tabs.

24. A securing tape as set forth in claim 22 wherein said fixed ends of said first and second tabs are sufficiently close to each other so that said first and second tabs curl around an article which is secured by said first and second tabs.

25. A securing tape as set forth in claim 21 wherein said fixed end of said second tab is integrally attached to said first tab and extends away from its fixed end in a direction which is opposite to the direction in which said first tab extends away from its fixed end.

26. A securing tape as set forth in claim 25 wherein said first tab includes a portion which curls around an article which is secured by said first and second tabs.

27. A securing tape as set forth in claim 25 wherein said first tab comprises two spaced portions on opposite sides of said second tab.

* * * * *